US011207458B2

(12) United States Patent
Locke et al.

(10) Patent No.: US 11,207,458 B2
(45) Date of Patent: Dec. 28, 2021

(54) PRESSURE-OPERATED SWITCH

(71) Applicant: KCI Licensing, Inc., San Antonio, TX (US)

(72) Inventors: Christopher Brian Locke, Bournemouth (GB); Benjamin Andrew Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 273 days.

(21) Appl. No.: 15/534,124

(22) PCT Filed: Jan. 29, 2016

(86) PCT No.: PCT/US2016/015842
§ 371 (c)(1),
(2) Date: Jun. 8, 2017

(87) PCT Pub. No.: WO2016/126560
PCT Pub. Date: Aug. 11, 2016

(65) Prior Publication Data
US 2018/0311419 A1 Nov. 1, 2018

Related U.S. Application Data

(60) Provisional application No. 62/110,822, filed on Feb. 2, 2015.

(51) Int. Cl.
*A61M 5/00* (2006.01)
*A61M 1/00* (2006.01)
(Continued)

(52) U.S. Cl.
CPC .......... *A61M 1/90* (2021.05); *A61F 13/00068* (2013.01); *A61M 1/74* (2021.05);
(Continued)

(58) Field of Classification Search
CPC ........ A61M 5/00; A61M 25/00; A61M 31/00; A61M 25/16; A61M 39/02; A61M 27/00;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for corresponding PCT/US2016/015842 dated Jun. 7, 2016.

(Continued)

*Primary Examiner* — Tatyana Zalukaeva
*Assistant Examiner* — Ilya Y Treyger

(57) ABSTRACT

Systems, methods, and apparatuses for regulating the delivery of negative-pressure therapy are described. The system includes a negative-pressure source, an energy source, and a switch. The switch can include a first conductor electrically coupled to the negative-pressure source, a second conductor electrically coupled to the energy source, and a diaphragm having a first position electrically coupling the first conductor to the second conductor and a second position separated from the first conductor and the second conductor. The diaphragm is configured to move between the first position and the second position in response to a differential between a control pressure and a therapy pressure.

20 Claims, 14 Drawing Sheets

(51) Int. Cl.
*H01H 35/34* (2006.01)
*H01H 35/26* (2006.01)
*H01H 35/40* (2006.01)
*A61F 13/00* (2006.01)
*A61M 39/24* (2006.01)
*A61M 25/00* (2006.01)
*A61M 31/00* (2006.01)
*A61M 25/16* (2006.01)
*A61M 39/02* (2006.01)
*A61M 27/00* (2006.01)
*A61K 9/02* (2006.01)
*H01H 35/28* (2006.01)

(52) U.S. Cl.
CPC ........ *A61M 39/24* (2013.01); *H01H 35/2614* (2013.01); *H01H 35/346* (2013.01); *H01H 35/40* (2013.01); *A61M 2039/242* (2013.01); *A61M 2039/246* (2013.01); *A61M 2205/3341* (2013.01); *A61M 2205/3355* (2013.01); *H01H 35/28* (2013.01)

(58) Field of Classification Search
CPC ...... A61M 2039/242; A61M 2039/246; A61M 2205/3341; A61M 2205/3355; A61K 9/02
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,552,284 B1 | 4/2003 | Drago |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 8,961,146 B2 * | 2/2015 | Phillips ................ B67D 1/0004 417/36 |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |

(56) References Cited

U.S. PATENT DOCUMENTS

| | | |
|---|---|---|
| 2002/0143286 A1 | 10/2002 | Tumey |
| 2014/0163491 A1 | 6/2014 | Schuessler et al. |
| 2015/0080788 A1 | 3/2015 | Blott et al. |

FOREIGN PATENT DOCUMENTS

| | | | |
|---|---|---|---|
| AU | 755496 B2 | | 12/2002 |
| CA | 2005436 A1 | | 6/1990 |
| CN | 201204154 Y | | 3/2009 |
| DE | 26 40 413 A1 | | 3/1978 |
| DE | 43 06 478 A1 | | 9/1994 |
| DE | 29 504 378 U1 | | 9/1995 |
| EP | 0100148 A1 | | 2/1984 |
| EP | 0117632 A2 | | 9/1984 |
| EP | 0161865 A2 | | 11/1985 |
| EP | 0358302 A2 | | 3/1990 |
| EP | 1018967 A1 | | 7/2000 |
| GB | 692578 A | | 6/1953 |
| GB | 2 195 255 A | | 4/1988 |
| GB | 2 197 789 A | | 6/1988 |
| GB | 2 220 357 A | | 1/1990 |
| GB | 2 235 877 A | | 3/1991 |
| GB | 2 329 127 A | | 3/1999 |
| GB | 2 333 965 A | | 8/1999 |
| GB | 2483281 A | | 3/2012 |
| JP | 4129536 B2 | | 8/2008 |
| SE | WO 00/31766 | * | 11/1998 |
| SG | 71559 | | 4/2002 |
| WO | 80/02182 A1 | | 10/1980 |
| WO | 87/04626 A1 | | 8/1987 |
| WO | 90/010424 A1 | | 9/1990 |
| WO | 93/009727 A1 | | 5/1993 |
| WO | 94/020041 A1 | | 9/1994 |
| WO | 96/05873 A1 | | 2/1996 |
| WO | 97/18007 A1 | | 5/1997 |
| WO | 99/13793 A1 | | 3/1999 |
| WO | 0031766 A1 | | 6/2000 |
| WO | 2009016603 A2 | | 2/2009 |
| WO | 2010017484 A2 | | 2/2010 |
| ZA | WO 2009/016603 | * | 8/2007 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds" Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and

(56) References Cited

OTHER PUBLICATIONS

Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Chinese Office Action for Corresponding Application No. 2016800152266, dated Oct. 8, 2019.
Chinese Second Office Action for Corresponding Application No. 201680015226.6, dated Jul. 30, 2020.

\* cited by examiner

PRESSURE-OPERATED SWITCH

This application is the National Stage of International Application No. PCT/US2016/015842, entitled "Pressure-Operated Switch," filed Jan. 29, 2016 and claims the benefit of U.S. Provisional Patent Application No. 62/110,822, entitled "Pressure-Operated Switch," filed Feb. 2, 2015, all of which are incorporated herein by reference for all purposes.

TECHNICAL FIELD

The invention set forth in the appended claims relates generally to tissue treatment systems and more particularly, but without limitation, to a pressure switch and a negative-pressure therapy system incorporating a pressure switch.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with negative pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for controlling negative pressure in a negative-pressure therapy environment are set forth in the appended claims. Illustrative embodiments are also provided to enable a person skilled in the art to make and use the claimed subject matter. For example, a system for providing negative pressure therapy is described. The system may include a negative-pressure source, an energy source, and a switch. The switch may include a first conductor electrically coupled to the negative-pressure source and a second conductor electrically coupled to the energy source. The switch may also include a diaphragm having a first position electrically coupling the first conductor to the second conductor and a second position separated from the first conductor and the second conductor. The diaphragm can be configured to move between the first position and the second position in response to a differential between a control pressure and a therapy pressure.

Alternatively, other example embodiments may describe a pressure-actuated switch for operation by a negative-pressure system. The switch may include a first terminal electrically coupled to a negative-pressure source, a second terminal electrically coupled to an energy source, and a membrane configured to conduct electricity disposed proximate to the first terminal and the second terminal. The membrane may have a first position electrically coupling the first terminal to the second terminal and a second position separated from the first terminal and the second terminal. The membrane may be configured to move between the first position and the second position in response to a differential between an ambient pressure and a therapy pressure.

A method for regulating negative-pressure therapy is also described. A negative-pressure source may be provided, and an energy source may be provided. A switch may be fluidly coupled to the negative-pressure source and configured to regulate a therapy pressure of the negative-pressure therapy. The switch may include a first conductor electrically coupled to the negative-pressure source, a second conductor electrically coupled to the energy source, and an actuator disposed proximate to the first conductor and the second conductor and configured to conduct electricity. The actuator may have a first position electrically coupling the first conductor to the second conductor and a second position separated from the first conductor and the second conductor. The actuator may be configured to move between the first position and the second position in response to a differential between an ambient pressure and a therapy pressure. The negative-pressure source may be operated to move the actuator between the first and second positions.

A regulator for controlling negative-pressure therapy is also described. The regulator may include a supply chamber adapted to be fluidly coupled to a dressing and a charging chamber configured to be fluidly coupled to a negative-pressure source and to the supply chamber through a port. A first terminal may be configured to be electrically coupled to the negative-pressure source and a second terminal may be configured to be electrically coupled to an energy source. A membrane may be coupled to the charging chamber, disposed proximate to the first terminal and the second terminal, and operable to conduct electricity. The membrane may have a first position electrically coupling the first terminal to the second terminal and a second position separated from the first terminal and the second terminal. The membrane may be operable to reciprocate between the first position and the second position to control operation of the negative-pressure source and fluid communication through the port based on a differential between an ambient pressure and a therapy pressure.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
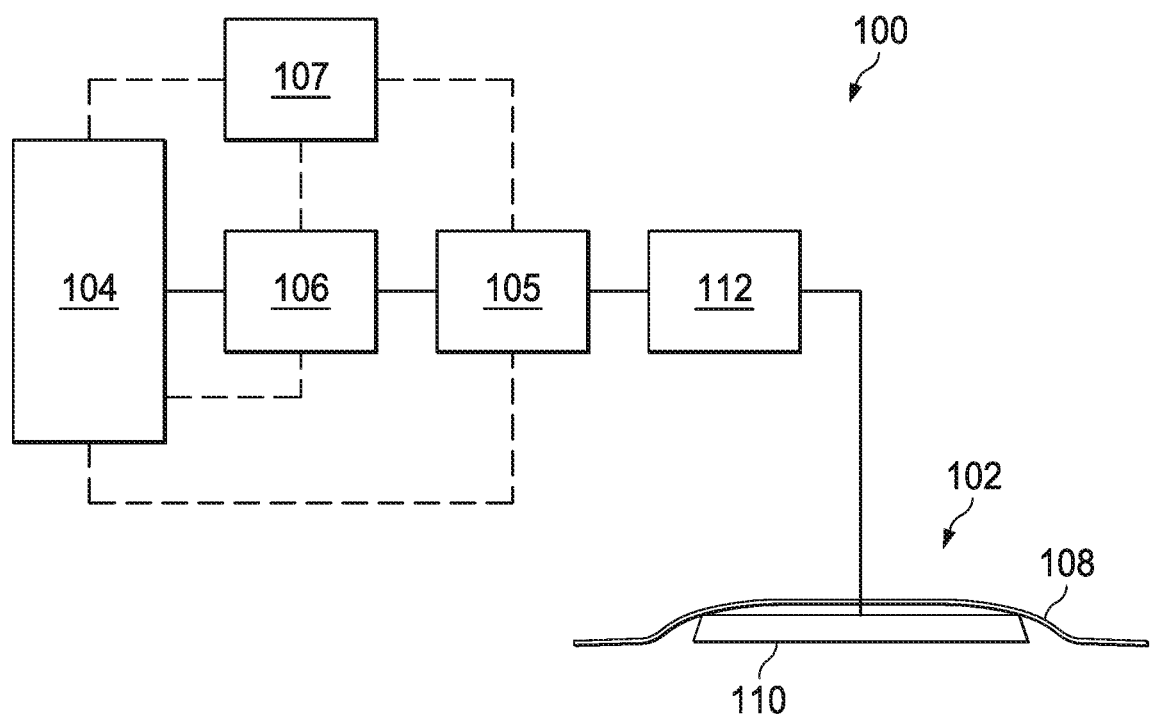
FIG. 1 is a functional block diagram of an example embodiment of a negative-pressure therapy system incorporating a pressure switch that can regulate pressure in accordance with this specification.

FIG. 1 is a simplified functional block diagram of an example embodiment of a therapy system 100 that can provide negative-pressure therapy in accordance with this specification. The therapy system 100 may include a dressing and a negative-pressure source. For example, a dressing 102 may be fluidly coupled to a negative-pressure source 104, as illustrated in FIG. 1. A dressing generally includes a cover and a tissue interface. The dressing 102, for example, includes a cover 108, and a tissue interface 110. The therapy system 100 may also include a fluid container, such as a container 112, coupled to the dressing 102 and to the negative-pressure source 104.

A pressure switch, such as the switch 105, or a regulator or controller, such as a regulator 106, or both the switch 105 and the regulator 106 may also be fluidly coupled to the dressing 102 and the negative-pressure source 104. In some embodiments, a source of electric potential, such as an energy source 107, may be electrically coupled to one or more of the negative-pressure source 104, the switch 105, and the regulator 106. In some embodiments, the switch 105 and the regulator 106 may be combined in a regulator assembly. In other embodiments, the switch 105, the regulator 106, and the negative-pressure source 104 may be combined in a negative-pressure assembly. In still other embodiments, the switch 105, the negative-pressure source 104, and the container 112 may be combined in a negative-pressure assembly.

In general, components of the therapy system 100 may be coupled directly or indirectly. For example, the negative-pressure source 104 may be directly coupled to the regulator 106 and indirectly coupled to the dressing 102 through the regulator 106. Components may be fluidly coupled to each other to provide a path for transferring fluids (i.e., liquid and/or gas) between the components.

In some embodiments, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected in container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of negative-pressure therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of about 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, some or all of the cover 108 may be coated with an acrylic adhesive having a coating weight between about 25-65 grams per meter squared (g.s.m.). Thicker adhesives, or combinations of adhesives, may be applied to improve the seal and reduce leaks. Other example embodiments of an attachment device may include a double-sided tape, paste, hydrocolloid, hydrogel, silicone gel, or organogel.

A source of electric potential, such as the energy source 107, may be a source of electrical energy, such as a battery or an electrical wall outlet, for example. In some embodiments, a source of electric potential may be a source of alternating current or a source of direct current. A source of electric potential may be configured to receive alternating current and convert the alternating current to direct current. In other embodiments, a source of electric potential may be configured to receive direct current and convert the direct current to alternating current. A source of electric potential may also include a transformer configured to step up or step down the voltage received from and provided by the source of electric potential.

The container 112 may be representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The therapy system 100 of FIG. 1 may solve some of the cost and complexity concerns associated with negative-pressure therapy. For example, the therapy system 100 may include a mechanical regulator, such as the regulator 106, and a pressure-actuated switch, such as the switch 105. The regulator 106 and the switch 105 can reduce the complexity of a negative-pressure therapy system while providing desired fluid flow rates, an ability to manage fluids, and customization of negative-pressure therapy without relying on software.

In some embodiments, a diaphragm can transform a pressure differential into movement to open and close an electric circuit. For example, a diaphragm can be configured to be responsive to a pressure differential between the atmospheric pressure and a control pressure. In a negative-pressure therapy system, for example, the control pressure may be a regulated pressure or a wound pressure, depending on the configuration of the negative-pressure therapy system. The diaphragm can also be configured to conduct electricity. In some embodiments, for example, the diaphragm may be conductive or doped with a conductive material, may have a conductive coating, or conductive contacts may be inserted or otherwise coupled to the diaphragm. Movement of the diaphragm can open and close a circuit, which can be used to provide input to feedback systems or as a controller to operate a pump or other negative-pressure source, for example.

Figure 2A:
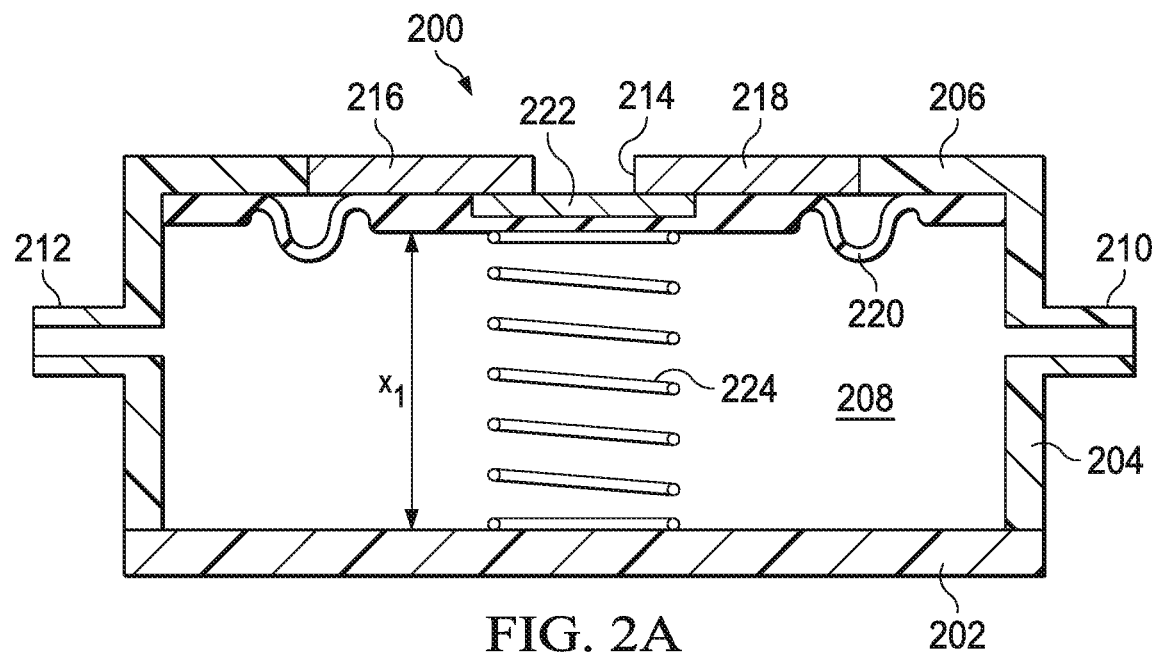
FIG. 2A is a schematic sectional diagram of an example embodiment of the pressure switch of FIG. 1.

FIG. 2A is a schematic diagram illustrating additional details that may be associated with an example embodiment of a switch 200 that may be used with the therapy system 100 of FIG. 1. The switch 200 may be an example embodiment of the switch 105. The switch 200 of FIG. 2A is illustrated in a closed position. As shown in FIG. 2A, the switch 200 may include an end wall 202, one or more side walls 204, and an end wall 206. In some embodiments, the end wall 202 may be circular. The side wall 204 may be a tubular wall and have a first end coupled to a periphery of the end wall 202. In some embodiments, the side wall 204 may have a length extending away from the end wall 202. The end wall 206 may also be circular. In some embodiments, the end wall 206 may be positioned over the end wall 202 and may have a periphery coupled to a second end of the side wall 204. The second end of the side wall 204 may be on an opposite end from the first end of the side wall 204. The end wall 202, the end wall 206, and the side wall 204 may be collectively referred to as a housing. In some embodiments, the housing may form a chamber 208, and the chamber 208 may be fluidly isolated from the ambient environment.

In some embodiments, the switch 200 may further include a fluid inlet 210 and a fluid outlet 212. The fluid inlet 210 may be coupled to the housing. For example, in the embodiment of FIG. 2A, the fluid inlet 210 is coupled to the side wall 204. The fluid inlet 210 may provide a path for fluid communication between the ambient environment and the chamber 208. In some embodiments, the fluid inlet 210 may be coupled to a tube or other fluid conductor to provide a fluid path between the chamber 208 and another device, such as the dressing 102.

In some embodiments, the fluid outlet 212 may also be coupled to the housing. For example, the fluid outlet 212 may be coupled to the side wall 204, as illustrated in the example embodiment of FIG. 2A. In some embodiments, the fluid outlet 212 may be positioned on an opposite side of the housing from the fluid inlet 210. In other embodiments, the fluid inlet 210 and the fluid outlet 212 may be proximate to one another. The fluid outlet 212 may provide a path for fluid communication between the ambient environment and the chamber 208. In some embodiments, the fluid outlet 212 may be coupled to a tube or other fluid conductor so that the chamber 208 may be in fluid communication with another device, such as the negative-pressure source 104, through the fluid outlet 212.

In some embodiments, the end wall 206 may include an opening 214. The opening 214 may be proximate to a center of the end wall 206. In other embodiments, the opening 214 may not be proximate to the center of the end wall 206. The opening 214 may permit fluid communication through the end wall 206 with the chamber 208. In some embodiments, the opening 214 may be circular. In other embodiments, the opening 214 may be square, triangular, or amorphously shaped.

In some embodiments, the end wall 206 may have a first conductor, such as a first terminal 216 and a second conductor, such as a second terminal 218. The first terminal 216 and the second terminal 218 may be positioned on opposite sides of the opening 214. The first terminal 216 and the second terminal 218 may be electro-mechanical devices that allow joining of electrical circuits with a mechanical assembly, such as electrical connectors or terminals that connect two or more wires to a single connection point. In some embodiments, the first terminal 216 and the second terminal 218 may not be electrically coupled to each other through the end wall 206.

In some embodiments, an actuator, such as a flexible membrane or a diaphragm 220, may be disposed in the chamber 208. The diaphragm 220 may be positioned proximate to the end wall 206. The diaphragm 220 may have peripheral portions coupled to the side wall 204, and the diaphragm 220 may extend across the chamber 208. If the diaphragm 220 is coupled to the side wall 204, the diaphragm 220 may fluidly isolate the chamber 208 from the ambient environment. In some embodiments, the diaphragm 220 may be a disc with a diameter larger than the width of the opening 214 in the end wall 206. In other embodiments, the diaphragm 220 may have other shapes configured to fluidly isolate the opening 214 from the chamber 208. In some embodiments, the diaphragm 220 may be formed from a silicone material and may have a hardness rating between about 30 Shore A and about 50 Shore A.

In some embodiments, the diaphragm 220 may include a third conductor, such as a contact 222. The contact 222 may be positioned on a side of the diaphragm 220 facing the opening 214 in the end wall 206. In some embodiments, the contact 222 may be positioned proximate to the first terminal 216 and the second terminal 218. For example, the contact 222 may be positioned on a top of the diaphragm 220 so that deflection of the diaphragm 220 in response to a pressure differential across the diaphragm 220 may cause the contact 222 to physically touch the first terminal 216 and the second terminal 218. In some embodiments, the contact 222 may be positioned in a center of the diaphragm 220 and have a width that permits the contact 222 to straddle the opening 214. The contact 222 may have an electrically conductive periphery. The contact 222 may be a resistor, such as a wire, a plate, or another device formed of an electrically conductive material, such as aluminum, copper, gold, or the like. In some embodiments, the contact 222 may be an integral member of the diaphragm 220. For example, the diaphragm 220 may be formed of a conductive material, may be coated in a conductive material, or may be doped in a conductive material.

In some embodiments, the actuator may be biased. For example, the actuator may have elastic properties biasing the actuator to a particular position. For example, the actuator may be formed of a thin metal, elastomer, rubber, or other elastically deformable material, which may be deformed in response to a pressure differential and return to its natural position if the pressure differential is removed. The actuator may also include a biasing member operatively coupled to the diaphragm 220. For example, the biasing member may be a spring, such as a spring 224 disposed in the chamber 208. The spring 224 may have a first end disposed against the end wall 202 and a second end operatively coupled to the diaphragm 220. In some embodiments, the first end of the spring 224 may be coupled to the end wall 202. The spring 224 may be compressed between the end wall 202 and the diaphragm 220. In some embodiments, the spring 224 may have a relaxed length $X_1$ if the spring 224 is neither extended nor compressed, so that spring 224 does not exert a spring force. In some embodiments, the spring 224 may be slightly compressed even in the closed position of the switch 200, as shown in FIG. 2A. If the spring 224 is compressed, the spring 224 may exert a force on the diaphragm 220, urging the diaphragm 220 into contact with the end wall 206 and the contact 222 into an electrical coupling with the first terminal 216 and the second terminal 218.

A pressure differential across the diaphragm 220 may also operate on the diaphragm 220. For example, a difference in pressures between the chamber 208 and the ambient environment of the switch 200 can cause the diaphragm 220 to move or deflect. The pressure differential across the diaphragm 220 may also be represented as an equivalent differential force on the diaphragm 220. The pressure in the chamber 208 may also be referred to as a control pressure. If the control pressure in the chamber 208 and the pressure in the ambient environment are substantially equal, the differential force may be approximately zero. If the control pressure in the chamber 208 is less than the ambient pressure, for example, if the switch 200 is being used to provide reduced-pressure therapy, the differential force may act to urge the diaphragm 220 away from the end wall 206.

Figure 2B:
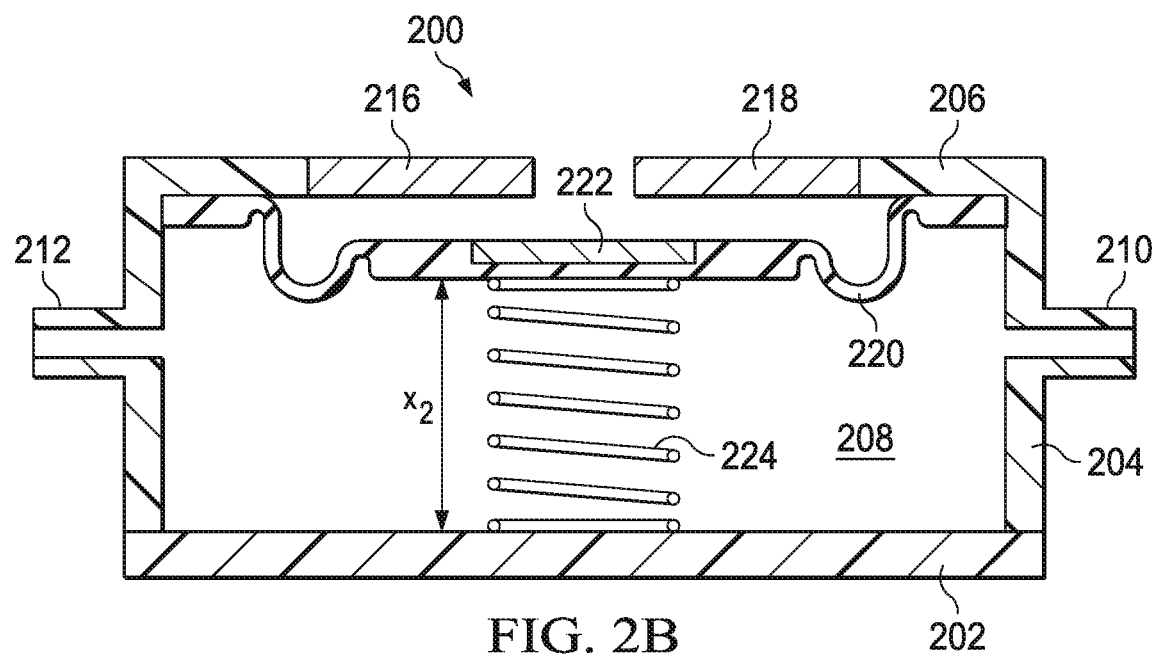
FIG. 2B is a schematic sectional diagram illustrating additional details that may be associated the switch of FIG. 2A in a second position.

In general, a differential force acting on the diaphragm 220 acts in opposition to any force applied to the diaphragm 220 by the spring 224. If the differential force is less than the force of the spring 224 acting on the diaphragm 220, the diaphragm 220 may be urged into contact with the end wall 206 and the contact 222 may be urged into an electrical coupling with the first terminal 216 and the second terminal 218, as shown in FIG. 2A. If the differential force is greater than the force on the spring 224, the diaphragm 220 may be urged away from the end wall 206, and the contact 222 may be urged out of contact with the first terminal 216 and the second terminal 218. As shown in FIG. 2B, if the differential force is greater than the spring force, the diaphragm 220 may compress the spring 224 against the end wall 202 to open the switch 200. In some embodiments, the spring 224 may have a length X, in the open position of the switch 200 illustrated in FIG. 2B. In some embodiments, the length $X_2$ of the spring 224 may be less than the length $X_1$ of the spring 224.

In some embodiments, the switch 200 may be fluidly coupled to the negative-pressure source 104. For example, the negative-pressure source 104 may be fluidly coupled to the fluid outlet 212, and the dressing 102 may be fluidly coupled to the fluid inlet 210. The negative-pressure source 104 may be operatively coupled to the energy source 107 for operation of the negative-pressure source 104. In some embodiments, an electric circuit coupling the negative-pressure source 104 to the energy source 107 may include the first terminal 216 and the second terminal 218. For example, electric current may flow from the energy source 107 to the first terminal 216, and electric current may flow from the second terminal 218 to the negative-pressure source 104. If the first terminal 216 and the second terminal 218 are electrically coupled, such as through the contact 222, then electric current may flow through the switch 200 from the energy source 107 to the negative-pressure source 104, powering the negative-pressure source 104 for operation. If the first terminal 216 and the second terminal 218 are not electrically coupled, electric current may not flow through the switch 200 from the energy source 107 to the negative-pressure source 104, and the negative-pressure source 104 may not operate.

In some embodiments, if the control pressure is about equal to a threshold pressure, which may be the ambient pressure, the contact 222 may be urged into an electrical coupling with the first terminal 216 and the second terminal 218. A threshold pressure may be a negative pressure that is less than the therapy pressure at which activation of the negative-pressure source may be desired. For example, without a pressure differential across the diaphragm 220, the spring 224 can press the contact 222 against the first terminal 216 and the second terminal 218. In response, an electric current may flow between the first terminal 216 and the second terminal 218 through the contact 222. In some embodiments, the negative-pressure source 104 may receive the electric current, and the electric current may power a pump of the negative-pressure source 104 to draw fluid from the dressing 102 through the fluid inlet 210 and the fluid outlet 212. As fluid is drawn from the chamber 208 through the fluid outlet 212, the pressure in the chamber 208 may decrease. Decreasing the pressure in the chamber 208 may increase the differential force. In some embodiments, if the pressure in the chamber 208 is decreased until the control pressure is about equal to a therapy pressure, the differential force may overcome the force of the spring 224, moving the diaphragm 220 away from the end wall 206 and breaking the electrical coupling between the first terminal 216 and the second terminal 218 through the contact 222. The therapy pressure may be a pressure at which negative-pressure therapy is performed. For example, the therapy pressure may be a pressure less than the ambient pressure at which the tissue site experiences the benefits of negative-pressure therapy. The therapy pressure can be about −125 mm Hg. In other embodiments, the therapy pressure may be a greater negative pressure or a lesser negative pressure depending on the desired effects of treatment.

In response, the electric current may no longer flow between the first terminal 216 and the second terminal 218. If the negative-pressure source 104 is electrically coupled to the energy source 107 through the switch 200, stopping the flow of electric current can remove the source of power from the pump of the negative-pressure source 104, stopping the operation of the negative-pressure source 104.

If the pressure in the chamber 208 increases toward the ambient pressure, the spring 224, compressed to the $X_2$ position of FIG. 2B, may overcome the differential force, urging the diaphragm 220 into contact with the end wall 206. In response, the electrical connection between the negative-pressure source 104 and the source of electric potential may be reestablished and electric current may flow between the first terminal 216 and the second terminal 218 through the contact 222, allowing the negative-pressure source 104 to operate and draw fluid from the chamber 208 through the fluid outlet 212.

Figure 2C:
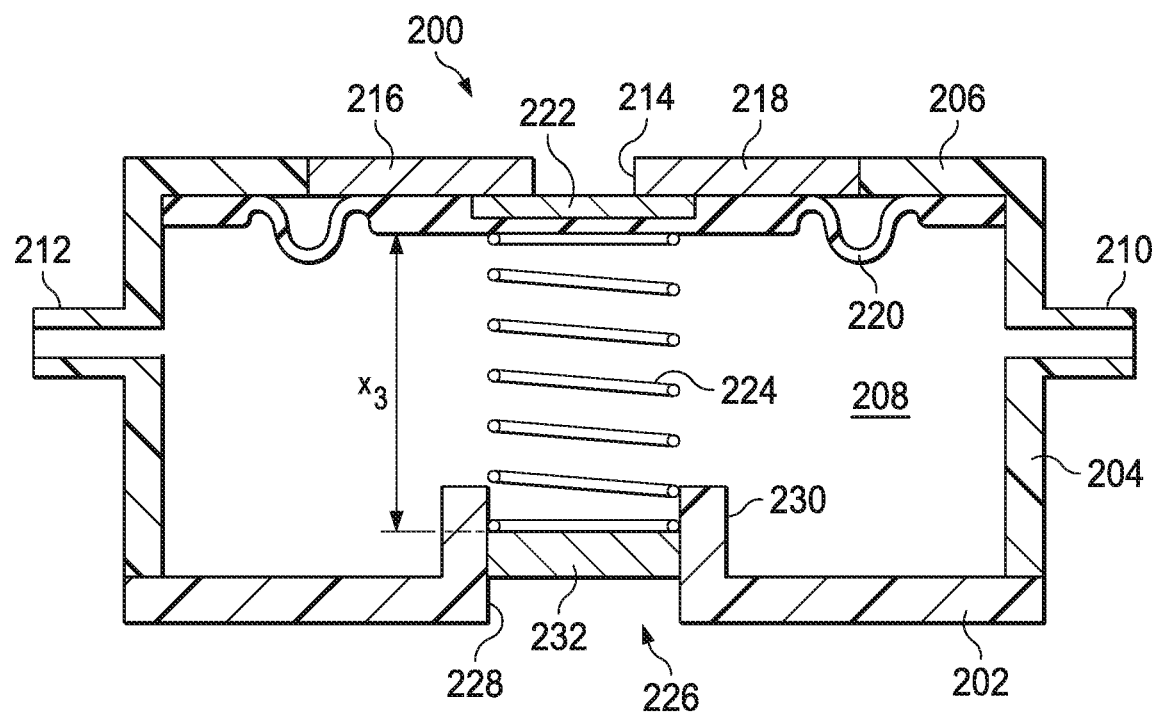
FIG. 2C is a schematic sectional diagram illustrating additional details that may be associated with another example embodiment of the switch of FIG. 1.

FIG. 2C is a schematic diagram illustrating additional details that may be associated with another embodiment of the switch 200. As shown in FIG. 2C, the switch 200 may include a calibration assembly 226. In some embodiments, the calibration assembly 226 may include an opening 228 formed in the end wall 202. The opening 228 may be coaxial with the opening 214 and the spring 224. The calibration assembly 226 may also include an annular wall 230 coupled to the end wall 202 and extending into the chamber 208. In some embodiments, the annular wall 230 may circumscribe the opening 228. The annular wall 230 may have a thread formed on a surface of the annular wall 230 proximate to the opening 228. The calibration assembly 226 may further include a calibrator 232. The calibrator 232 may be a disc having an outer diameter surface that is threaded to mate with the thread of the annular wall 230. The calibrator 232 may be operatively coupled to the first end of the spring 224 so that, if the calibrator 232 is threaded through the annular wall 230, the length of the spring 224 may be changed. For example, in FIG. 2C, the calibrator 232 is threaded into the annular wall 230 so that the calibrator 232 is about halfway between an outer surface of the end wall 202 and an end of the annular wall 230. The position of the calibrator 232 may compress the spring 224 against the diaphragm 220. In some embodiments, the spring 224 may be compressed to the length $X_3$ by the calibrator 232. Because the force exerted by the spring 224 is proportional to the distance the spring 224 is compressed from the relaxed state, controlling the amount of compression of the spring 224 with the calibrator 232 may allow the pressure at which the differential force overcomes the force of the spring 224 to be controlled. In this manner, the force of the spring 224 may be varied to calibrate the switch 200 to open and close at particular pressures in the chamber 208. For example, the spring 224 may be compressed by the calibrator 232 to increase the magnitude of the pressure differential across the diaphragm 220 needed to overcome the force of the spring 224 and open the switch 200.

Figure 3A:
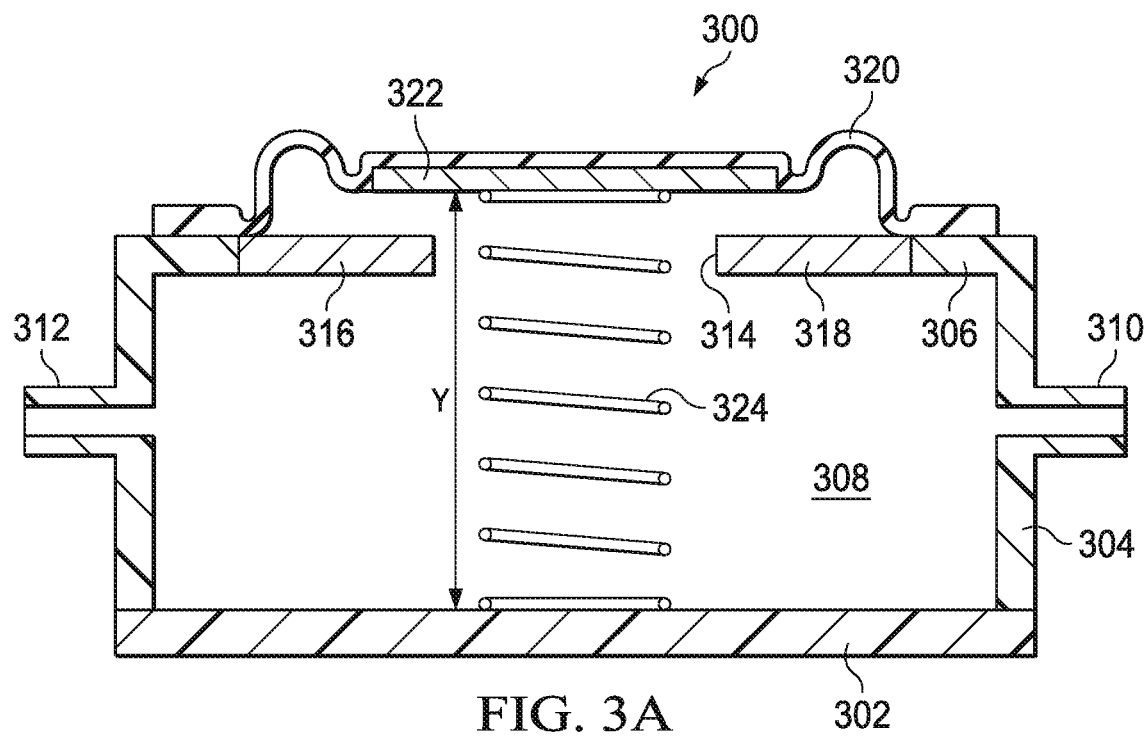
FIG. 3A is a schematic sectional diagram of another example embodiment of the switch FIG. 1.

FIG. 3A is a schematic diagram illustrating additional details that may be associated with an example embodiment of a switch 300 the therapy system 100 of FIG. 1. For example, the switch 300 may be an example of the switch 105 illustrated in FIG. 1. In some embodiments, the switch 300 may be similar to and operate as described above with respect to the switch 200. Similar elements may have similar reference numbers indexed to 300. As shown in FIG. 3A, the switch 300 may include an end wall 302, one or more side walls 304, and an end wall 306. In some embodiments, the end wall 302 may be circular. The side wall 304 may be a tubular wall and have a first end coupled to a periphery of the end wall 302. In some embodiments, the side wall 304 may have a length extending away from the end wall 302. The end wall 306 may also be circular. In some embodiments, the end wall 306 may be positioned over the end wall 302 and may have a periphery coupled to a second end of the side wall 304. The second end of the side wall 304 may be on an opposite end from the first end of the side wall 304. In some embodiments, the end wall 302, the side wall 304, and the end wall 306 may collectively be referred to as a housing. The housing may form a chamber 308. In some embodiments, the chamber 308 may be fluidly isolated from the ambient environment.

In some embodiments, the switch 300 may further include a fluid inlet 310 and a fluid outlet 312. The fluid inlet 310 may be coupled to the housing. For example, in the embodiment of FIG. 3A, the fluid inlet 310 is coupled to the side wall 304. The fluid inlet 310 may provide a path for fluid communication between the ambient environment and the chamber 308. In some embodiments, the fluid inlet 310 may be coupled to a tube or other mechanism so that the chamber 308 may be in fluid communication with another device, such as the dressing 102, through the fluid inlet 310.

In some embodiments, the fluid outlet 312 may also be coupled to the housing. For example, in the embodiment of FIG. 3A, the fluid outlet is coupled to the side wall 304. The fluid outlet 312 may be positioned on an opposite side of the switch 300 from the fluid inlet 310. In other embodiments, the fluid inlet 310 and the fluid outlet 312 may be proximate to one another. The fluid outlet 312 may provide a path for fluid communication between the ambient environment and the chamber 308. In some embodiments, the fluid outlet 312 may be coupled to a tube or other mechanism so that the chamber 308 may be in fluid communication with another device, such as the negative-pressure source 104, through the fluid outlet 312.

In some embodiments, the end wall 306 may include an opening 314. The opening 314 may be proximate to a center of the end wall 306. In other embodiments, the opening 314 may not be proximate to the center of the end wall 306. In some embodiments, the opening 314 may permit fluid communication with the chamber 308 through the end wall 306.

In some embodiments, the end wall 306 may have a first conductor, such as a first terminal 316 and a second conductor, such as a second terminal 318. The first terminal 316 and the second terminal 318 may be positioned on opposite sides of the opening 314. The first terminal 316 and the second terminal 318 may be electro-mechanical devices that allow joining of electrical circuits with a mechanical assembly, such as electrical connectors or terminals that connect two or more wires to a single connection point. In some embodiments, the first terminal 316 and the second terminal 318 may not be electrically coupled to each other through the end wall 306.

In some embodiments, an actuator, such as a flexible membrane or a diaphragm 320, may be coupled to the end wall 306. The diaphragm 320 may be positioned proximate to the end wall 306. The diaphragm 320 may have peripheral portions coupled to the end wall 306, and the diaphragm 320 may extend across the opening 314. In some embodiments, the diaphragm 320 may fluidly isolate the chamber 308 from the ambient environment. For example, a difference in the pressures in the chamber 308 and the ambient environment may cause deflection of the diaphragm 320. In some embodiments, the diaphragm 320 may be a disc with a diameter larger than the diameter of the opening 314 in the end wall 306. In other embodiments, the diaphragm 320 may have other shapes configured to fluidly isolate the opening 314 from the chamber 308. In some embodiments, the diaphragm 320 may be formed from a silicone material, and the diaphragm 320 may have a hardness rating between about 30 Shore A and about 50 Shore A.

In some embodiments, the diaphragm 320 may include a third conductor, such as a contact 322. The contact 322 may be positioned on a side of the diaphragm 320 facing the end wall 306. In some embodiments, the contact 322 may be positioned proximate to the first terminal 316 and the second terminal 318. For example, the contact 322 may be positioned on a bottom of the diaphragm 320 so that deflection of the diaphragm 320 in response to a pressure differential across the diaphragm 320 may cause the contact 322 to physically touch the first terminal 316 and the second terminal 318. In some embodiments, the contact 322 may be positioned in a center of the diaphragm 320 and have a width that permits the contact 322 to straddle the opening 314. The contact 322 may have an electrically conductive periphery and an electrically insulated center portion. The contact 322 may be a resistor, such as a wire, a plate, or another device formed of an electrically conductive material, such as aluminum, copper, gold, or the like. In some embodiments, the contact 322 may be an integral member of the diaphragm 320. For example, the diaphragm 320 may be formed of a conductive material, may be coated in a conductive material, or may be doped in a conductive material.

In some embodiments, the actuator may be biased. For example, the actuator may have elastic properties biasing the actuator to a particular position. For example, the actuator may be formed of a thin metal, elastomer, rubber, or other elastically deformable material, which may be deformed in response to a pressure differential and return to its natural position if the pressure differential is removed. The actuator may also include a biasing member, such as a spring 324, may be disposed in the chamber 308. The spring 324 may have a first end proximate to the end wall 302 and a second end operatively coupled to the diaphragm 320. In some embodiments, the first end of the spring 324 may be coupled to the end wall 302, and the spring 324 may have a length Y in a relaxed position. In the relaxed position, the spring 324 may be neither extended nor compressed so that spring 324 does not exert a spring force.

A differential force may operate on the diaphragm 320. The differential force may be a force generated by a difference in pressures between the chamber 308 and the ambient environment of the switch 300. The pressure in the chamber 308 may also be referred to as a control pressure. If the control pressure in the chamber 308 and the pressure in the ambient environment are substantially equal, the differential force may be approximately zero. If the control pressure in the chamber 308 is less than the ambient pressure, the differential force may act to urge the diaphragm 320 toward the end wall 306.

In some embodiments, the switch 300 may be fluidly coupled to the negative-pressure source 104. For example, the negative-pressure source 104 may be fluidly coupled to the fluid outlet 312, and the dressing 102 may be fluidly coupled to the fluid inlet 310. In some embodiments, the negative-pressure source 104 may be operatively coupled to the energy source 107 for operation of the negative-pressure source 104. The negative-pressure source 104 may receive electric current from the energy source 107 and may include a controller. The controller may be electrically coupled to the first terminal 316 and the second terminal 318. In some embodiments, the controller may operate the negative-pressure source 104 to draw fluid from the chamber 308. If the first terminal 316 and the second terminal 318 are electrically coupled, such as through the contact 322, then electric current may flow to the controller in the form of an electric signal. If the first terminal 316 and the second terminal 318 are not electrically coupled, electric current may not flow to the controller. In some embodiments, the controller may operate the negative-pressure source 104 until the controller receives an electric signal from the switch 300.

In some embodiments, if the control pressure is about equal to the threshold pressure, which may be the ambient pressure, the contact 322 may be urged out of the electrical coupling with the first terminal 316 and the second terminal 318 by the spring 324. For example, without a pressure differential across the diaphragm 320, the spring 324 can press the contact 322 away from the first terminal 316 and the second terminal 318. In response, the controller of the negative-pressure source 104 may not receive the electric signal and, in response, operate the negative-pressure source 104 to draw fluid from the tissue site through the fluid inlet 310 and out the fluid outlet 312. As fluid is drawn from the chamber 308 through the fluid outlet 312, the pressure in the chamber 308 may decrease and approach the therapy pressure. Decreasing the pressure in the chamber 308 may increase the differential force. In some embodiments, if the pressure in the chamber 308 is about the therapy pressure, the differential force may overcome the force of the spring 324, moving the diaphragm 320 toward the end wall 306 and forming an electrical coupling between the first terminal 316 and the second terminal 318 through the contact 322. Electrically coupling the first terminal 316 and the second terminal 318 through the contact 322 generates the electric signal. In some embodiments, the spring 324 may not be electrically conductive. In response to receiving the electric signal, the controller of the negative-pressure source 104 may stop operation of the negative-pressure source 104.

Figure 3B:
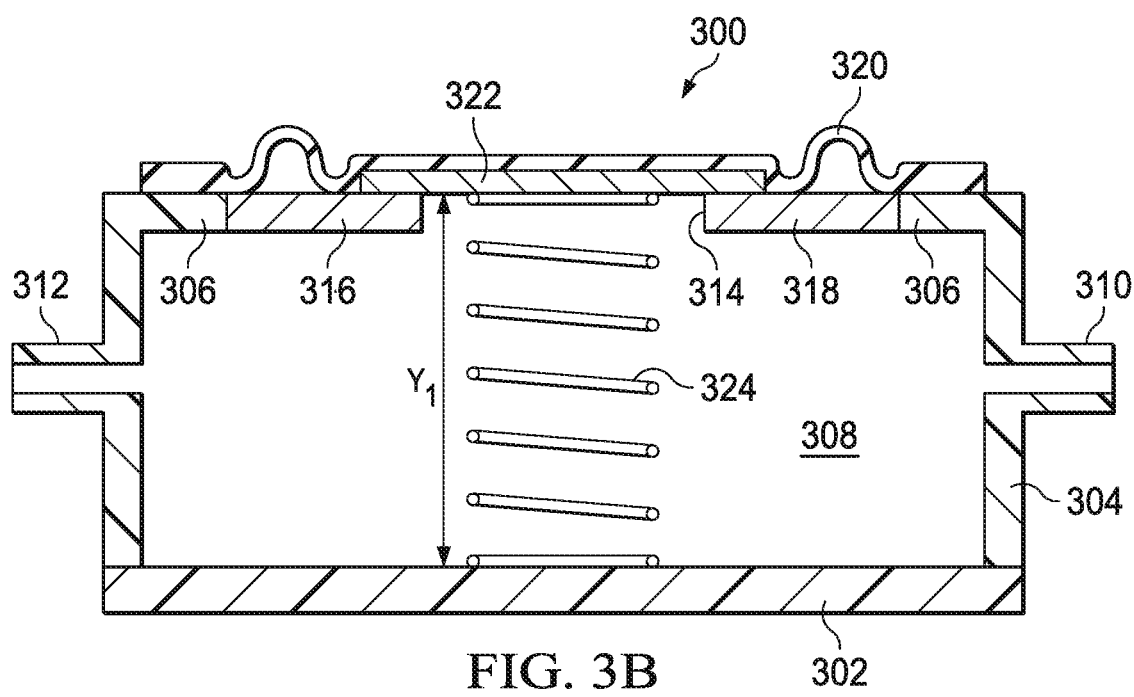
FIG. 3B is a schematic sectional diagram illustrating additional details that may be associated with the switch of FIG. 3A in a second position.

If the pressure in the chamber 308 increases, that is, moves toward the ambient pressure from the therapy pressure, the spring 324, compressed to the $Y_1$ position of FIG. 3B, may overcome the differential force, urging the diaphragm 320 out of contact with the end wall 306. In response, the electrical coupling between the first terminal 316 and the second terminal 318 is removed, and the electric signal is stopped. If the controller of the negative-pressure source 104 stops receiving the electric signal, the controller of the negative-pressure source 104 may operate the negative-pressure source 104 and draw fluid from the chamber 308 through the fluid outlet 312.

Figure 3C:
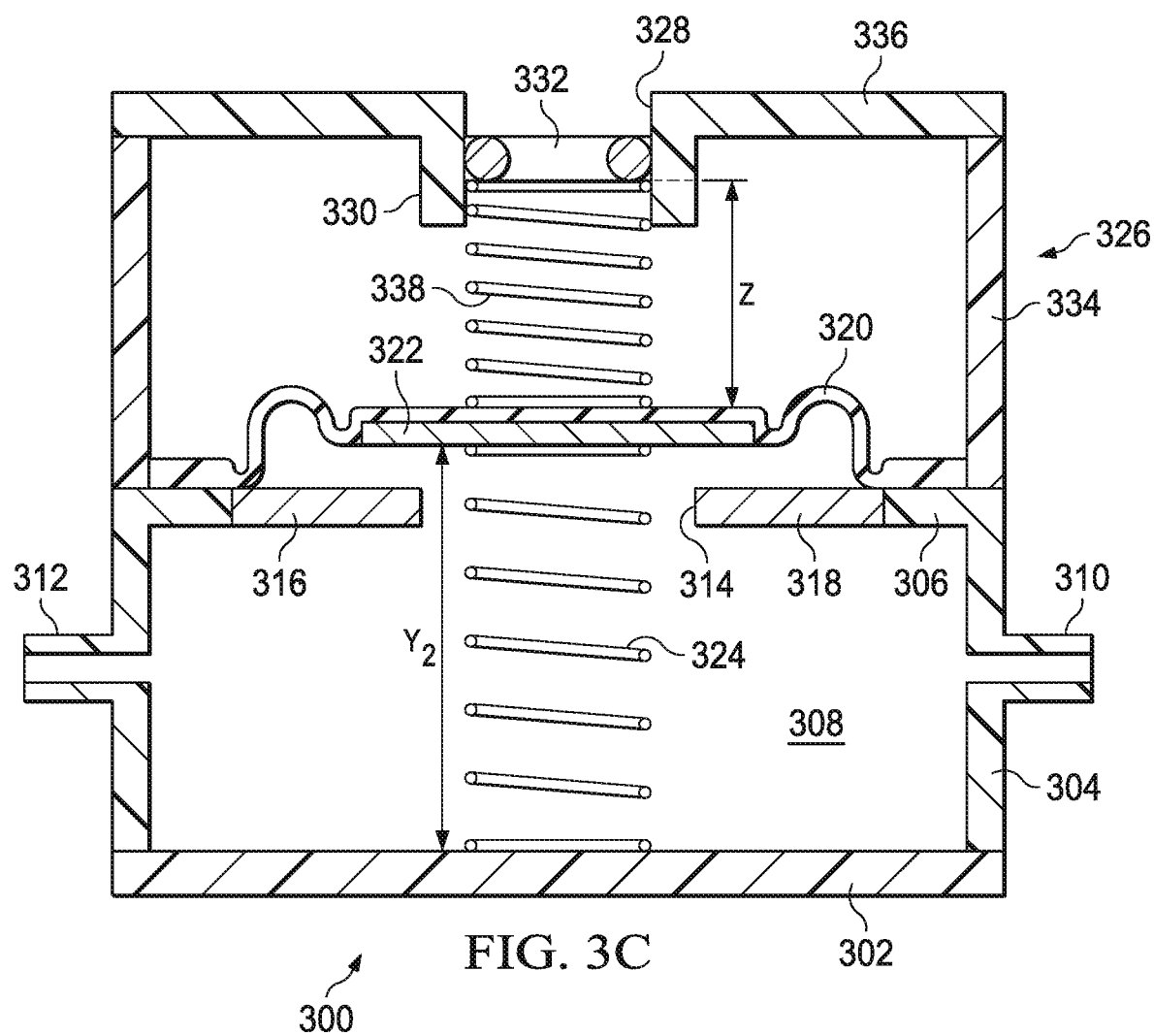
FIG. 3C is a schematic sectional diagram illustrating additional details that may be associated with another example embodiment of the switch of FIG. 1.

FIG. 3C is a schematic diagram illustrating additional details that may be associated with another embodiment of the switch 300. As shown in FIG. 3C, the switch 300 may include a calibration assembly 326. The calibration assembly 326 may include a side wall 334. The side wall 334 may be an annular wall coupled to the end wall 306. In some embodiments, the calibration assembly 326 may further include an end wall 336. The end wall 336 may be positioned over the end wall 306 and coupled to the side wall 334. The end wall 336 may have an opening 328 formed proximate to a center of the end wall 336. In some embodiments, the opening 328 may be coaxial with the opening 314 in the end wall 306.

A wall 330 may be coupled to the end wall 336 proximate to the opening 328 and extend toward the opening 314. In some embodiments, the wall 330 may be annular and may circumscribe the opening 328. The wall 330 may have a thread formed on a surface proximate to the opening 328.

The calibration assembly 326 may also include a calibrator 332. The calibrator 332 may be disc having a thread formed on an outer diameter surface of the calibrator 332. In some embodiments, the thread may mate with the thread formed on the wall 330, allowing the calibrator 332 to be threaded into the wall 330. The calibrator 332 may be a ring. In some embodiments, fluid communication through the opening 328 may be possible through the calibrator 332. For example, ambient pressure may be present on both sides of the end wall 336.

The calibration assembly 326 may also include a calibration spring 338. The calibration spring 338 may have a first end positioned adjacent to the calibrator 332 and a second end operatively coupled to the diaphragm 320. In some embodiments, the second end of the calibration spring 338 may contact the diaphragm 320 on an opposite side of the diaphragm 320 from the spring 324. In some embodiments, the calibration spring 338 may exert a force in response to movement of the calibration spring 338 from a relaxed position. If the calibration spring 338 is disposed in the switch 300, the calibration spring 338 may be moved from the relaxed position so that the calibration spring 338 may have a length Z. If the calibration spring 338 is compressed to the length Z, the calibration spring 338 may exert a calibration force urging the diaphragm 320 toward the end wall 306. Generally, the force exerted on the diaphragm 320 may be proportional to a distance the calibration spring 338 is moved from the relaxed position. In some embodiments, the force of the spring 324 and the force of the calibration spring 338 may urge the diaphragm 320 in opposite directions.

In some embodiments, the calibration spring 338 may exert a force that assists the differential force in urging the diaphragm 320 into contact with the end wall 306. The force exerted by the calibration spring 338 may be used to calibrate the switch 300 to the desired therapy pressure. For example, the switch 300 may be tested to determine if the switch 300 supplies negative pressure at a desired therapy pressure with no calibration force. If the switch 300 fails to provide the therapy pressure, the calibrator 332 may be threaded into the wall 330 to increase the calibration force applied by the calibration spring 338. In other embodiments, if the switch 300 has already been calibrated, the switch 300 may be tested to determine if the switch 300 operates at a desired therapy pressure. If the switch 300 does not operate at the desired therapy pressure, the calibrator 332 may be threaded out of the wall 330 to decrease the calibration force applied by the calibration spring 338, thereby increasing the required differential force to overcome the force of the spring 324.

Figure 4:
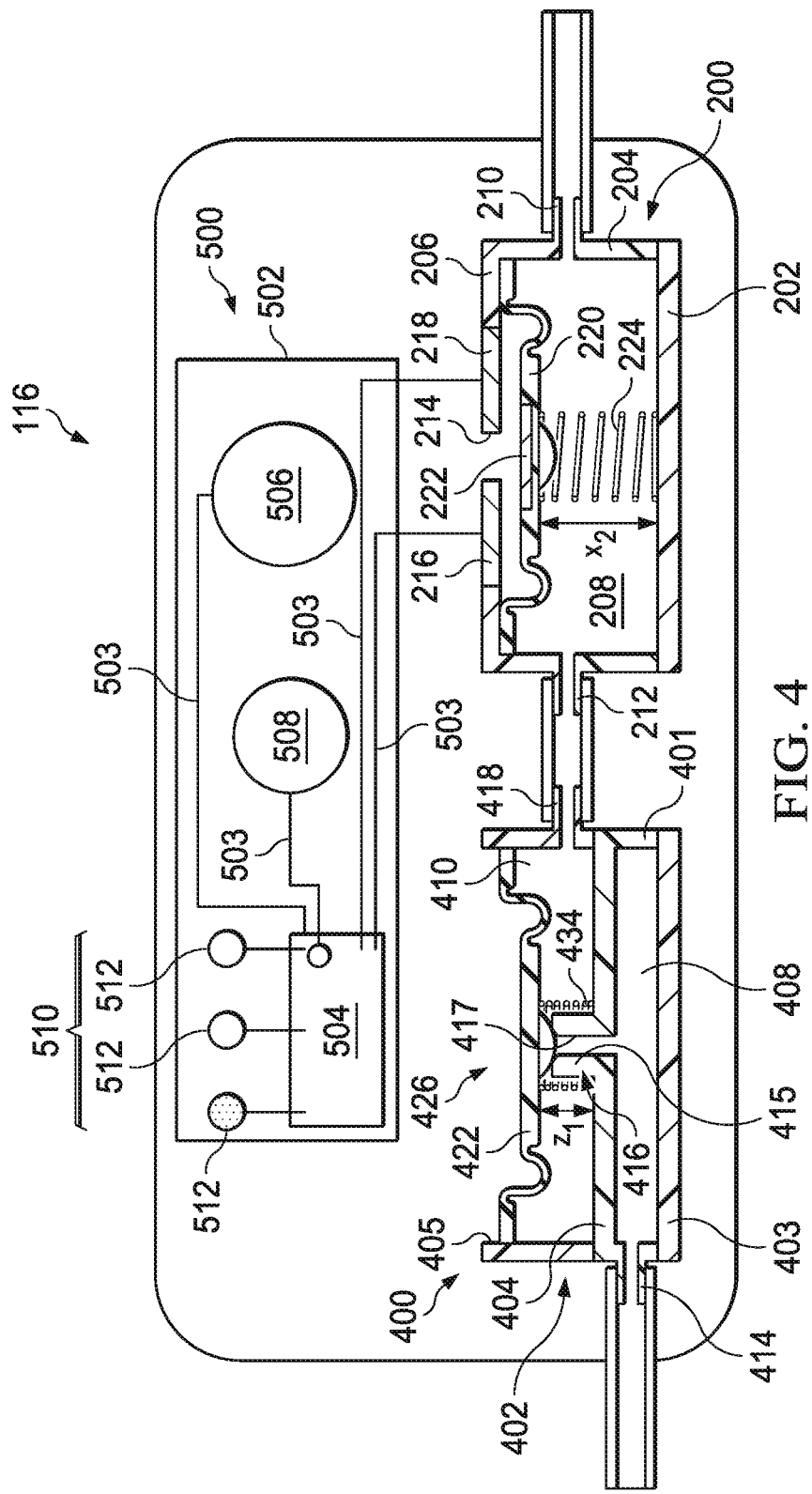
FIG. 4 is a schematic diagram illustrating additional details that may be associated with an example embodiment of a regulator assembly having the switch of FIG. 2A.

FIG. 4 is a schematic illustration of a regulator assembly 116 that may be used with some embodiments of the therapy system 100 of FIG. 1. The regulator assembly 116 may include a housing adapted to protect operational elements of the regulator assembly 116 from the ambient environment. The regulator assembly 116 may be fluidly coupled to the dressing 102 and the negative-pressure source 104. In some embodiments, the regulator assembly 116 may control the negative-pressure source 104. As shown in FIG. 4, the regulator assembly 116 may include the switch 200 of FIG. 2A and FIG. 2B, a mechanical regulator 400, and an electronic assembly 500.

The mechanical regulator 400 may include a housing 402 and a regulator valve 426. The housing 402 may have an end wall 403, one or more side walls 401, and an open end 405 opposite the end wall 403. The side walls 401 may be coupled to peripheral portions of and generally perpendicular to the end wall 403.

The housing 402 may be partitioned by a wall 404 to form a charging chamber 408 and a supply chamber 410. In some embodiments, the charging chamber 408 may adjoin the supply chamber 410, being disposed between the end wall 403, the wall 404, and the side walls 401. The supply chamber 410 may be disposed between the charging chamber 408 and the open end 405. For example, in FIG. 4, the wall 404 separates the charging chamber 408 and the supply chamber 410. The supply chamber 410 may be bounded by the wall 404, the side walls 401, and the open end 405. The wall 404 may be coupled to the side walls 401 of the housing 402 at peripheral portions of the wall 404. In some embodiments, no fluid communication may occur between the charging chamber 408, and the supply chamber 410 at the locations where the wall 404 couples to the housing 402.

The housing 402 and the wall 404 may be formed of a material having a sufficient strength to resist collapse if a negative pressure is supplied to the charging chamber 408 and the supply chamber 410, such as metals, hard plastics, or other suitable materials. For example, the housing 402 and the wall 404 may resist collapse if a negative pressure of about 150 mm Hg (−150 mm Hg gauge pressure) is supplied to the charging chamber 408 and the supply chamber 410. In other exemplary embodiments, the housing 402 and the wall 404 may resist collapse if a negative pressure of about 600 mm Hg (−600 mm Hg gauge pressure) is supplied to the charging chamber 408 and the supply chamber 410.

The charging chamber 408 may include a source port 414 and a charging port 416. The source port 414 may be disposed in one of the side walls 401 of the charging chamber 408 and may be fluidly coupled to the charging chamber 408. In some embodiments, the source port 414 may be configured to be fluidly coupled to a supply of negative pressure, such as an electric pump, a manual pump, or wall-suction source, for example. In some embodiments, the source port 414 may be fluidly coupled to a wall-suction source by a conduit or tube. A one-way valve may be disposed in the source port 414 and oriented to prevent fluid flow into the charging chamber 408 through the source port 414 and permit fluid flow out of the charging chamber 408 through the source port 414.

In some embodiments, the charging port 416 may be disposed in the wall 404, as shown in the illustrative embodiment of FIG. 4. The charging port 416 may fluidly couple the charging chamber 408 and the supply chamber 410. In some embodiments, the charging port 416 may have a cylindrical wall 415 and a central passage 417 that extends between the charging chamber 408 and the supply chamber 410. The cylindrical wall 415 may include a portion extending into the supply chamber 410 from the wall 404 so that the charging port 416 terminates near a center portion of the open end 405. In some embodiments, the charging port 416 may be disposed in other locations of the wall 404, and the charging port 416 may have a valve seat on the distal end. The valve seat may provide a tapered or beveled edge proximate to the central passage 417 of the charging port 416.

The supply chamber 410 may include a supply port 418. In some embodiments, the supply port 418 may be fluidly coupled to the supply chamber 410 and provide an interface to the supply chamber 410. For example, the supply port 418 may be configured to be coupled to a tube, which can be coupled to an upstream component, such as the switch 200. A one-way valve may be disposed in the supply port 418 and oriented to permit fluid flow into the supply chamber 410 through the supply port 418 and prevent fluid flow out of the supply chamber 410 through the supply port 418.

In some embodiments, a fluid path between the charging port 416 and the supply chamber 410 may be controlled by the regulator valve 426. The regulator valve 426 may include a valve member 422 and a regulator spring 434. The regulator valve 426 can be coupled to the open end 405 and operably associated with the charging port 416 to regulate fluid communication between the charging chamber 408 and the supply chamber 410. The regulator valve 426 can be biased to either open or close the charging port 416. The regulator valve 426 may be coupled to ends of the side walls 401 of the housing 402, opposite the end wall 403 of the housing 402. In some embodiments, the regulator valve 426 may substantially limit or prevent fluid communication through the open end 405 of the housing 402.

In some embodiments, the valve member 422 may be a flexible membrane, such as a diaphragm. The valve member 422 may have a generally disc-like shape with a diameter larger than the diameter of the open end 405. In other embodiments, the valve member 422 may have a shape matched to fluidly isolate the open end 405, for example, square, rectangular, ovoid, triangular, or amorphous shapes. The valve member 422 may have peripheral portions coupled to the side walls 401, and the valve member 422 may extend across the open end 405. If the valve member 422 is coupled to the side walls 401, the valve member 422 may fluidly isolate the supply chamber 410 from the ambient environment surrounding the mechanical regulator 400. For example, a difference in the pressures in the supply chamber 410 and the ambient environment may cause deflection of the valve member 422. In some embodiments, the valve member 422 may be formed from a silicone material. The valve member 422 may have a hardness rating between about 40 Shore A and about 50 Shore A.

In some embodiments, the valve member 422 may include an enlarged portion configured to engage the valve seat. The valve member 422 may be positioned so that the enlarged portion of the valve member 422 may engage a beveled edge of the valve seat of the charging port 416 in a closed position. If engaged in such a manner, the valve member 422 can substantially prevent fluid communication through the central passage 417 of the charging port 416.

The regulator spring 434 may be disposed on the charging port 416 so that the regulator spring 434 circumscribes the charging port 416. The regulator spring 434 may have a first end adjacent to the wall 404. In some embodiments, the first end of the regulator spring 434 may contact the wall 404 so that the regulator spring 434 may be compressed against the wall 404. A second end of the regulator spring 434 may be adjacent to the distal end of the charging port 416. The regulator spring 434 may have a length Z if in a relaxed position. In the relaxed position, the regulator spring 434 may be longer than the charging port 416.

In some embodiments, a differential force may operate on the valve member 422. The differential force may be a force generated by a difference in pressures between the supply chamber 410 and the ambient environment of the mechanical regulator 400. The pressure in the supply chamber 410 may also be referred to as a "supply pressure." If the supply pressure in the supply chamber 410 and the pressure in the ambient environment are substantially equal, the differential force may be approximately zero. If the supply pressure in the supply chamber 410 is less than the ambient pressure, for example, if the mechanical regulator 400 is being used to provide negative-pressure therapy, the differential force may act to urge the valve member 422 toward the distal end of the charging port 416.

In some embodiments, the regulator spring 434 may exert a force in response to movement of the regulator spring 434 from the relaxed position. If the regulator spring 434 is disposed in the supply chamber 410, the regulator spring 434 may be moved from the relaxed position so that the regulator spring 434 has a length $Z_1$. If the regulator spring 434 is compressed to the length $Z_1$, the regulator spring 434 may exert a regulator force urging the valve member 422 away from the valve seat 424 of the charging port 416. Generally, the regulator force exerted on the valve member 422 may be proportional to a distance the regulator spring 434 is moved from the relaxed position. Generally, the regulator spring 434 may be selected so that the differential force may overcome the regulator force if the supply pressure is about the therapy pressure. If the differential force overcomes the regulator force, the valve member 422 may contact the charging port 416 and prevent fluid communication through the charging port 416.

The electronic assembly 500 may include a printed circuit board (PCB) 502, a controller 504, a first battery 506, a second battery 508, and a lighting assembly 510. The printed circuit board 502 may be an electronic device having one or more electronic components communicatively coupled by conductive pathways 503. Generally, printed circuit boards may be formed of conductive and non-conductive laminar sheets that are chemically etched to create communicative couplings. Printed circuit boards may also include additional electronic components such as capacitors, resistors, or other active devices. In some embodiments, the printed circuit board 502 may include a power supply or electric potential source, such as the first battery 506 or the second battery 508. In other embodiments, the PCB 502 may be coupled to an external power source, such as the energy source 107. In some embodiments, the PCB 502 may include a visual device, such as the lighting assembly 510, an auditory device, such as a speaker or auditory pulse emitter, a tactile device, such as a moving protrusion, or an olfactory device. The printed circuit board 502 may further include an electronic storage device, such as a memory, a processing unit, and other devices configured to operate the electronic assembly 500.

In some embodiments, the lighting assembly 510 may include one or more light emitting diodes (LEDs) 512. Each LED 512 of the lighting assembly 510 may be a semiconductor light source that includes a chip of semiconducting material that is doped with impurities to create a p-n junction. Current may be supplied to the p-n junction, causing movement of electrons across the junction and the release of energy in the form of a photon. The photon may comprise visible light having a particular wavelength. The wavelength of the photons emitted by the LED 512 may be selected during manufacturing of the LED 512 so that the LED 512 may emit a desired color of light. In some embodiments, the LEDs 512 may be formed on the printed circuit board 502. In other embodiments, the LEDs 512 may be formed independently and later communicatively coupled to the printed circuit board 502. The LEDs 512 may be communicatively coupled to the controller 504 to receive a signal from the controller 504.

The first battery 506 and the second battery 508 may be single-cell voltage sources that may be coupled to the printed circuit board 502. In some embodiments, the first battery 506 and the second battery 508 may be replaceable. In other embodiments, the first battery 506 and the second battery 508 may be rechargeable and configured to receive a current or voltage from an external source. The first battery 506 and the second battery 508 may be further communicatively coupled to the LEDs 512 and the controller 504 to provide current to the LEDs 512 and the controller 504 for the operation thereof. In some embodiments, the controller 504 may be electrically coupled to the first terminal 216 and the second terminal 218 of the switch 200.

A controller, such as the controller 504, may be a computing device or system, such as a programmable logic controller, or a data processing system, for example. In some embodiments, a controller may be configured to receive input from one or more devices, such as a user interface, a sensor, or a flow meter, for example. A controller may receive input, such as an electrical signal, from an alternative source, such as through an electrical port, for example.

In some embodiments, a controller may be a data processing system. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

In some embodiments, a controller may be a programmable logic controller (PLC). A PLC may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

In some embodiments, the energy source 107 may be operatively coupled to the negative-pressure source 104, and the negative-pressure source may be fluidly coupled to the dressing 102 through the regulator 116. For example, the negative-pressure source 104 may be fluidly coupled to the source port 414, and the dressing 102 may be fluidly coupled to the fluid inlet 210. The supply port 418 may be fluidly coupled to the fluid outlet 212 so that the chamber 208 of the switch 200 is in fluid communication with the supply chamber 410. In some embodiments, the controller 504 may be electrically coupled to the first terminal 216 and the second terminal 218. The first battery 506 may be electrically coupled to the controller 504 to provide electric potential for one more of the LEDs 512. The second battery 508 may be electrically coupled to the controller 504 to provide electric potential to drive the signal received from the first terminal 216 and the second terminal 218. If the first terminal 216 and the second terminal 218 are electrically coupled, such as through the contact 222, then electric current may flow through the switch 200 to the controller 504, providing an electric signal to the controller 504. If the first terminal 216 and the second terminal 218 are not electrically coupled, the switch 200 will not provide an electric signal to the controller 504. In response to receiving an electric signal from the switch 200, the controller 504 may provide a visual indication of the state of operation of the therapy system 100 through the lighting assembly 510 and the LEDs 512.

In some embodiments, if the control pressure in the supply chamber 410 is about the ambient pressure, the valve member 422 may be urged out of contact with the distal end of the charging port 416, permitting fluid communication between the charging chamber 408 and the supply chamber 410. If the control pressure in the chamber 208 is about the ambient pressure, the contact 222 may be urged into electrical coupling with the first terminal 216 and the second terminal 218 by the spring 224. In response, the controller 504 may receive the electric signal from the switch 200 and operate one or more of the LEDs 512 of the lighting assembly 510. For example, one of the LEDs 512 may be lit to indicate that the pressure at the dressing 102 is about the ambient pressure.

Operation of the negative-pressure source 104 may cause the negative-pressure source 104 to draw fluid from the charging chamber 408 through the source port 414. In response, fluid may flow from the supply chamber 410 to the charging chamber 408 through the charging port 416. As fluid is drawn from the supply chamber 410, fluid may also be drawn from the chamber 208 through the fluidly coupled fluid outlet 212 and the supply port 418 and from the tissue site through the fluidly coupled fluid inlet 210. As fluid is drawn from the chamber 208 and the supply chamber 410, the pressure in the chamber 208 and the supply chamber 410 may decrease and approach the therapy pressure. Decreasing the pressure in the chamber 208 and the supply chamber 410 may increase the differential force in the switch 200 and the mechanical regulator 400, respectively. In some embodiments, if the pressure in the chamber 208 is about the therapy pressure, the differential force may overcome the force of the spring 224, moving the diaphragm 220 away from the end wall 206 and breaking the electrical connection between the first terminal 216 and the second terminal 218 through the contact 222. Similarly, if the pressure in the supply chamber 410 is about the therapy pressure, the differential force may overcome the force of the regulator spring 434, urging the valve member 422 into contact with the distal end of the charging port 416, stopping fluid communication between the supply chamber 410 and the charging chamber 408. In response, the controller 504 may operate a different combination of LEDs 512 of the lighting assembly 510 to provide the status of the therapy system 100. For example, the controller 504 may operate one or more of the LEDs 512 to indicate that the pressure at the dressing 102 is about the therapy pressure.

If the pressure in the chamber 208 increases, that is, moves toward the ambient pressure from the therapy pressure, the spring 224, compressed to the $X_2$ position of FIG. 2B, may overcome the differential force, urging the diaphragm 220 into contact with the end wall 206. In response, the controller 504 may operate the lighting assembly 510 to operate a different set of LEDs 512. For example, the controller 504 may illuminate one or more of the LEDs 512 to indicate that the tissue site is not receiving the therapy pressure. Similarly, if the pressure in the supply chamber 410 increases, that is, moves toward ambient pressure from the therapy pressure, the regulator spring 434, compressed to the $Z_1$ position of FIG. 4, may overcome the differential force, urging the valve member 422 away from the distal end of the charging port 416, allowing fluid communication through the mechanical regulator 400 to provide negative-pressure to the tissue site.

As described above, the regulator assembly 116 can control the supply of negative-pressure to the tissue site with the mechanical regulator 400 and provide an indication of the status of negative-pressure therapy with the switch 200 and the electronic assembly 500. The regulator assembly 116 provides a stand-alone component that may be used with a wall-suction source, a pump, or other vacuum device.

Figure 5A:
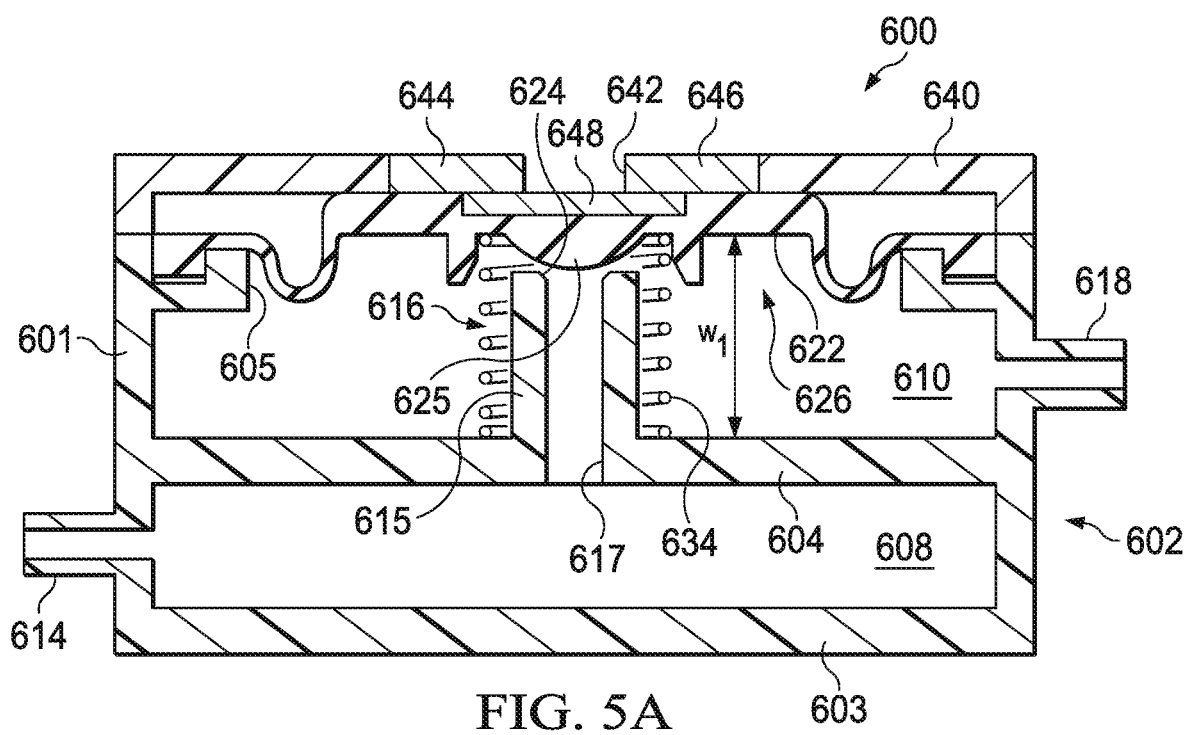
FIG. 5A is a schematic diagram illustrating additional details that may be associated with an example embodiment of a regulator switch that may be used with the negative-pressure therapy system of FIG. 1.

FIG. 5A is a sectional schematic view, illustrating a regulator switch 600 that may be used with the therapy system 100. The regulator switch 600 may combine features of the mechanical regulator 400 and the switch 200 of FIG. 4. For example, the regulator switch 600 may be similar to the mechanical regulator 400 of FIG. 4 and include components of the switch 200 of FIGS. 2A and 2B. In some embodiments, the regulator switch 600 may include a housing 602 and a regulator valve 626. The housing 602 may have an end wall 603, one or more side walls 601, and an open end 605 opposite the end wall 603. The side walls 601 may be coupled to peripheral portions of and generally perpendicular to the end wall 603.

The housing 602 may be partitioned by a wall 604 to form a charging chamber 608 and a supply chamber 610. In some embodiments, the charging chamber 608 may adjoin the supply chamber 610, being disposed between the end wall 603, the wall 604, and the side walls 601. The supply chamber 610 may be disposed between the charging chamber 608 and the open end 605. For example, in FIG. 5A, the wall 604 separates the charging chamber 608 and the supply chamber 610. The supply chamber 610 may be bounded by the wall 604, the side walls 601, and the open end 605. The wall 604 may be coupled to the side walls 601 of the housing 602 at peripheral portions of the wall 604. In some embodiments, no fluid communication may occur between the charging chamber 608 and the supply chamber 610 at the locations where the wall 604 couples to the housing 602.

The housing 602 and the wall 604 may be formed of a material having a sufficient strength to resist collapse if a negative pressure is supplied to the charging chamber 608 and the supply chamber 610, such as metals, hard plastics, or other suitable materials. For example, the housing 602 and the wall 604 may resist collapse if a negative pressure of about 150 mm Hg (−150 mm Hg gauge pressure) is supplied to the charging chamber 608 and the supply chamber 610. In other exemplary embodiments, the housing 602 and the wall 604 may resist collapse if a negative pressure of about 600 mm Hg (−600 mm Hg gauge pressure) is supplied to the charging chamber 608 and the supply chamber 610.

The charging chamber 608 may include a source port 614 and a charging port 616. The source port 614 may be disposed in one of the side walls 601 of the charging chamber 608 and may be fluidly coupled to the charging chamber 608. In some embodiments, the source port 614 may be configured to be fluidly coupled to a supply of negative pressure, such as an electric pump, a manual pump, or wall-suction source, for example. The source port 614 may be fluidly coupled to a wall-suction source by a conduit or tube. A one-way valve may be disposed in the source port 614 and oriented to prevent fluid flow into the charging chamber 608 through the source port 614 and permit fluid flow out of the charging chamber 608 through the source port 614.

In some embodiments, the charging port 616 may be disposed in the wall 604, as shown in the illustrative embodiment of FIG. 5A. The charging port 616 may fluidly couple the charging chamber 608 and the supply chamber 610. In some embodiments, the charging port 616 may have a cylindrical wall 615 and a central passage 617 that extends between the charging chamber 608 and the supply chamber 610. The cylindrical wall 615 may include a portion extending into the supply chamber 610 from the wall 604 so that the charging port 616 terminates near a center portion of the open end 605. In some embodiments, the charging port 616 may be disposed in other locations of the wall 604. The charging port 616 may have a valve seat 624 on the distal end. The valve seat 624 may provide a tapered or beveled edge proximate to the central passage 617 of the charging port 616.

The supply chamber 610 may include a supply port 618. In some embodiments, the supply port 618 may be fluidly coupled to the supply chamber 610 and provide an interface to the supply chamber 610. For example, the supply port 618 may be configured to be coupled to a tube, which can be coupled to a dressing or other upstream component. A one-way valve may be disposed in the supply port 618 and oriented to permit fluid flow into the supply chamber 610 through the supply port 618 and prevent fluid flow out of the supply chamber 610 through the supply port 618.

In some embodiments, a fluid path may be provided between the charging port 616 and the supply chamber 610, which may be controlled by the regulator valve 626. The regulator valve 626 may include a valve member 622 and a regulator spring 634. The regulator valve 626 can be coupled to the open end 605 and operably associated with the charging port 616 to regulate fluid communication between the charging chamber 608 and the supply chamber 610. The regulator valve 626 can be biased to either open or close the charging port 616. The regulator valve 626 may be coupled to ends of the side walls 601 of the housing 602, opposite the end wall 603 of the housing 602. In some embodiments, the regulator valve 626 may substantially limit or prevent fluid communication through the open end 605 of the housing 602.

In some embodiments, the valve member 622 may be a flexible membrane, such as a diaphragm. The valve member 622 may have a generally disc-like shape with a diameter larger than the diameter of the open end 605. In other embodiments, the valve member 622 may have a shape configured to fluidly isolate the open end 605, for example, square, rectangular, ovoid, triangular, or amorphous shapes. The valve member 622 may have peripheral portions coupled to the side walls 601, and the valve member 622 may extend across the open end 605. If the valve member 622 is coupled to the side walls 601, the valve member 622 may fluidly isolate the supply chamber 610 from the ambient environment surrounding the regulator switch 600. For example, a difference in the pressures in the supply chamber 610 and the ambient environment may cause deflection of the valve member 622. In some embodiments, the valve member 622 may be formed from a silicone material. The valve member 622 may have a hardness rating between about 60 Shore A and about 50 Shore A.

In some embodiments, the valve member 622 may include an enlarged portion 625 configured to engage the valve seat 624. The valve member 622 may be positioned so that the enlarged portion 625 of the valve member 622 may engage a beveled edge of the valve seat 624 of the charging port 616 in a closed position. If engaged in such a manner, the valve member 622 can substantially prevent fluid communication through the central passage 617 of the charging port 616.

The regulator spring 634 may be disposed on the charging port 616 so that the regulator spring 634 circumscribes the charging port 616. The regulator spring 634 may have a first end adjacent to the wall 604. In some embodiments, the first end of the regulator spring 634 may contact the wall 604 so that the regulator spring 634 may be compressed against the wall 604. A second end of the regulator spring 634 may be adjacent to the distal end of the charging port 616. The regulator spring 634 may have a length W if in a relaxed position. In the relaxed position, the regulator spring 634 may be longer than the charging port 616.

The regulator switch 600 may include an end wall 640. In some embodiments, the end wall 640 may be circular. The end wall 640 may be positioned over the end wall 603 and may have a periphery coupled to a second end of the side wall 601. The second end of the side walls 601 may be on an opposite end from the first end of the side wall 601.

In some embodiments, the end wall 640 may include an opening 642. The opening 642 may be proximate to a center of the end wall 640. In other embodiments, the opening 642 may not be proximate to the center of the end wall 640. In some embodiments, the end wall 640 may have a first conductor, such as a first terminal 644 and a second conductor, such as a second terminal 646. The first terminal 644 and the second terminal 646 may be positioned on opposite sides of the opening 642. The first terminal 644 and the second terminal 646 may be electro-mechanical devices that allow joining of electrical circuits with a mechanical assembly, such as electrical connectors or terminals that connect two or more wires to a single connection point. In some embodiments, the first terminal 644 and the second terminal 646 may not be electrically coupled to each other through the end wall 640.

In some embodiments, the valve member 622 may include a third conductor, such as a contact 648. The contact 648 may be positioned on a side of the valve member 622 facing the end wall 640. In some embodiments, the contact 648 may be positioned proximate to the first terminal 644 and the second terminal 646. For example, the contact 648 may be positioned on a top of the valve member 622 so that deflection of the valve member 622 in response to a pressure differential across the valve member 622 may cause the contact 648 to physically touch the first terminal 644 and the second terminal 646. In some embodiments, the contact 648 may be positioned in a center of the valve member 622. In some embodiments, the contact 648 may have an electrically conductive periphery. The contact 648 may be a resistor, such as a wire, a plate, or another device formed of an electrically conductive material, such as aluminum, copper, gold, or the like. In some embodiments, the contact 648 may be an integral to the valve member 622. For example, the valve member 622 may be formed of a conductive material, may be coated in a conductive material, or may be doped in a conductive material.

In some embodiments, a differential force may operate on the valve member 622. The differential force may be a force generated by a difference in pressures between the supply chamber 610 and the ambient environment of the regulator switch 600. The pressure in the supply chamber 610 may also be referred to as a supply pressure or the control pressure. If the supply pressure in the supply chamber 610 and the pressure in the ambient environment are substantially equal, the differential force may be approximately zero. If the supply pressure in the supply chamber 610 is less than the ambient pressure, for example, if the regulator switch 600 is being used to provide negative-pressure therapy, the differential force may act to urge the valve member 622 toward the distal end of the charging port 616.

In some embodiments, the regulator spring 634 may exert a force in response to movement of the regulator spring 634 from the relaxed position. If the regulator spring 634 is disposed in the supply chamber 610, the regulator spring 634 may be moved from the relaxed position so that the regulator spring 634 has a length $W_1$. If the regulator spring 634 is compressed to the length $W_1$, the regulator spring 634 may exert a regulator force urging the valve member 622 away from the valve seat 624 of the charging port 616, and the contact 648 may be urged into an electrical coupling with the first terminal 644 and the second terminal 646.

Generally, the regulator force exerted on the valve member 622 may be proportional to a distance the regulator spring 634 is moved from the relaxed position. Generally, the regulator spring 634 may be selected so that the differential force may overcome the regulator force if the supply pressure is about the therapy pressure. If the differential force overcomes the regulator force, the valve member 622 may contact the charging port 616 and prevent fluid communication through the charging port 616. In addition, the contact 648 may be moved out of the electrical coupling with the first terminal 644 and the second terminal 646.

Figure 5B:
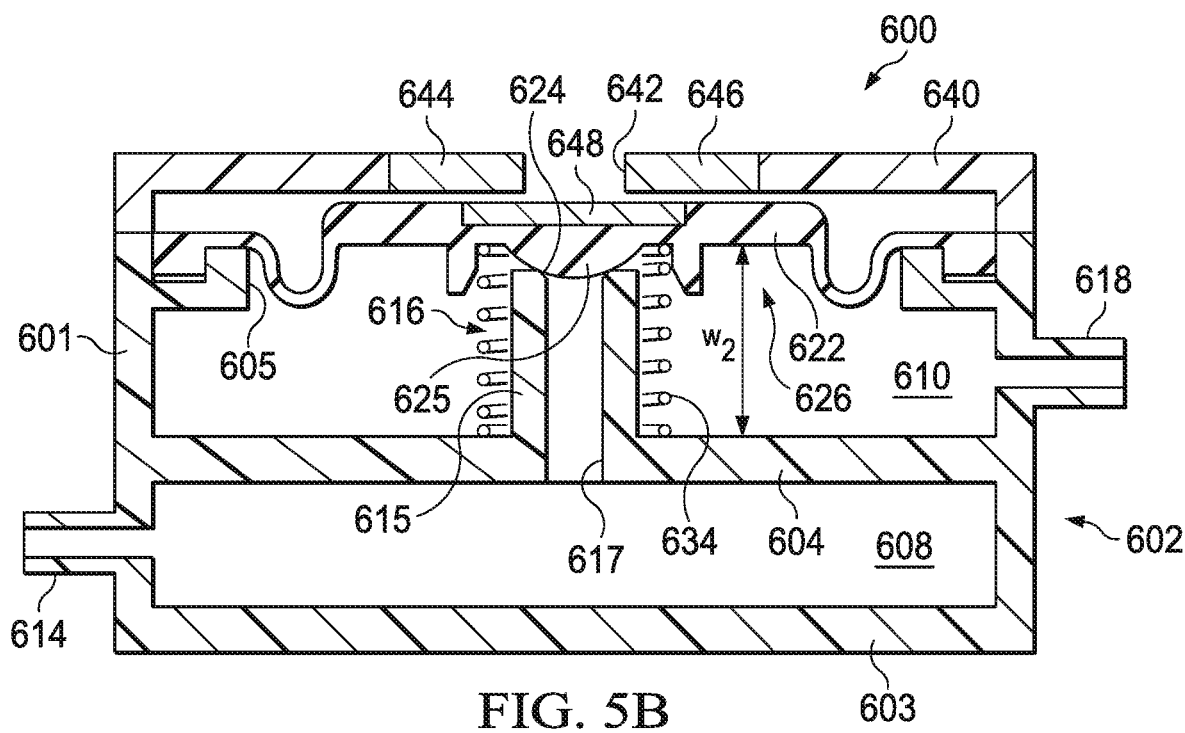
FIG. 5B is a schematic diagram illustrating additional details that may be associated with the regulator switch of FIG. 5A in a second position.

FIG. 5B is a schematic sectional view, illustrating additional details of the regulator switch 600 in a closed position. If the differential force is greater than the force of the regulator spring 634 acting on the valve member 622, the valve member 622 may be urged into contact with the distal end of the charging port 616 to prevent fluid communication through the charging port 616 in the closed position. In response, the regulator spring 634 may be compressed to a length $W_2$. In addition, the contact 648 may be urged away from and out of an electrical coupling with the first terminal 644 and the second terminal 646. If the differential force is less than the force of the regulator spring 634, the valve member 622 may be urged away from the distal end of the charging port 616 to permit fluid communication through the charging port 616 in the open position, shown in FIG. 5A. In addition, the contact 648 may be urged toward and into an electrical coupling with the first terminal 644 and the second terminal 646.

Figure 5C:
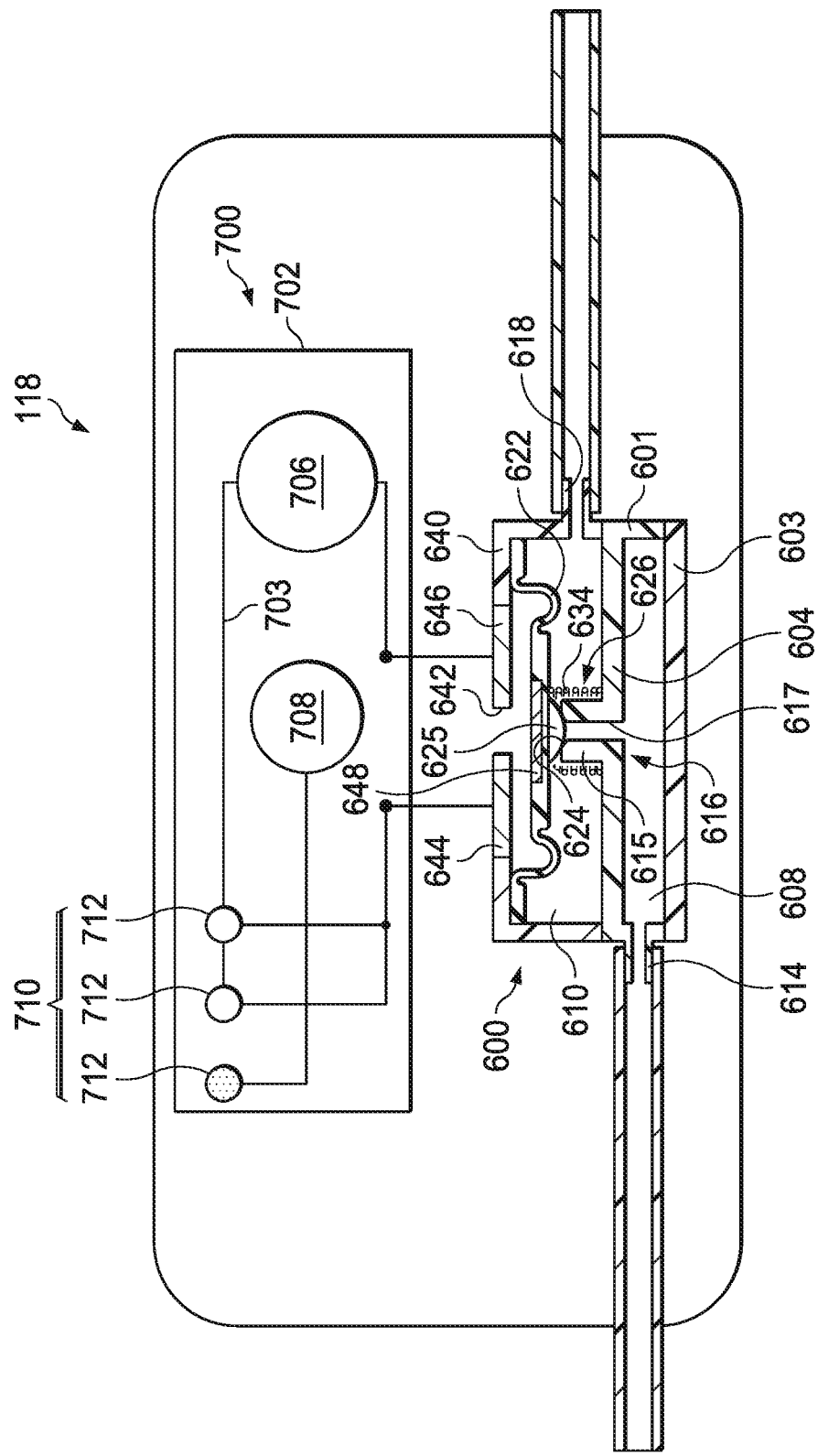
FIG. 5C is a schematic diagram illustrating additional details that may be associated with a regulatory assembly having the regulator switch of FIG. 5A.

FIG. 5C is a schematic view illustrating of a regulator assembly 118 that may be used with some embodiments of the therapy system 100 of FIG. 1. The regulator assembly 118 may include a housing adapted to protect operational elements of the regulator assembly 118 from the ambient environment. As shown in FIG. 5C, the regulator assembly 118 may include the regulator switch 600 of FIG. 5A and FIG. 5B and an electronic assembly 700.

The electronic assembly 700 may include a printed circuit board (PCB) 702, a first battery 706, a second battery 708, and a lighting assembly 710. The electronic assembly 700 may be similar to and operate as described above with respect to the electronic assembly 500. Similar elements may have similar reference numbers indexed to 700. The printed circuit board 702 may be an electronic device having one or more electronic components communicatively coupled by conductive pathways 703. In some embodiments, the printed circuit board 702 may include a power supply or electric potential source, such as the first battery 706 or the second battery 708, and a signal interface or indicator. In some embodiments, the signal interface may be a visual device, such as the lighting assembly 710, an auditory device, such as a speaker or auditory pulse emitter, a tactile device, such as a moving protrusion, or an olfactory device. The printed circuit board 702 may further include an electronic storage device, such as a memory, a processing unit, and other devices.

The first battery 706 and the second battery 708 may be further communicatively coupled to the lighting assembly 710 to provide current to the lighting assembly 710 for the operation thereof. In some embodiments, the lighting assembly 710, the first battery 706, and the second battery 708 may be electrically coupled to each other in an electric circuit. For example, the first battery 706 may be electrically coupled to the second terminal 646 and to one or more of the LEDs 712 of the lighting assembly 710. The LEDs 712 that are coupled to the first battery 706 may be further electrically coupled to the first terminal 644. The second battery 708 may be electrically coupled to the one or more of the LEDs 712. In some embodiments, the second battery 708 may supply a continuous current to at least one of the LEDs 712 of the lighting assembly 710. The first battery 706 may supply a current to the LEDs 712 of the lighting assembly 710 if the first terminal 644 and the second terminal 646 are electrically coupled through the contact 648.

In some embodiments, the negative-pressure source 104 may be fluidly coupled to the source port 614, and the dressing 102 may be fluidly coupled to the supply port 618. If the first terminal 644 and the second terminal 646 are electrically coupled, such as through the contact 648, then electric current may flow from the first battery 706 to the lighting assembly 710. If the first terminal 644 and the second terminal 646 are not electrically coupled, electric current may not flow from the first battery 706 to the lighting assembly 710. In some embodiments, if one or more of the LEDs 712 of the lighting assembly 710 are not illuminated, the pressure at the dressing 102 may be at the therapy pressure.

In some embodiments, if the control pressure in the supply chamber 610 is about the ambient pressure, the valve member 622 may be urged out of contact with the distal end of the charging port 616, permitting fluid communication between the charging chamber 608 and the supply chamber 610. If the control pressure in the chamber 608 is about the ambient pressure, the contact 648 may be urged into electrical coupling with the first terminal 644 and the second terminal 646 by the regulator spring 634. In response to the flow of electric current through the first terminal 644 and the second terminal 646, the lighting assembly 710 may be illuminated to provide an indication of the state of operation of the negative-pressure source 104. For example, one or more of the LEDs 712 may illuminate if current flows from the first battery 706 to the lighting assembly 710 through the regulator switch 600. In some embodiments, illumination of the one or more LEDs 712 electrically coupled to the first battery 706 may indicate that the pressure at the dressing 102 is not at the therapy pressure.

Figure 6A:
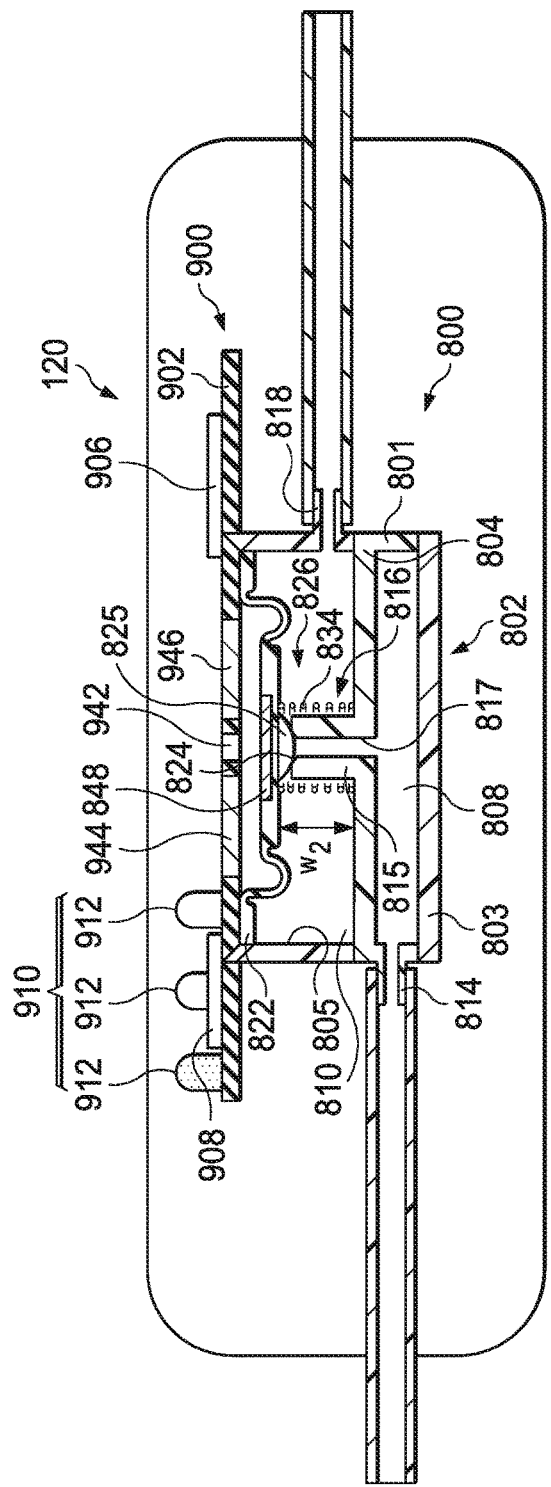
FIG. 6A is a schematic diagram illustrating additional details that may be associated with another embodiment of the regulator switch of FIG. 5A disposed in a regulator assembly.

FIG. 6A is a sectional schematic view illustration of another embodiment of a regulator assembly 120 that may be used with some embodiments of the therapy system 100 of FIG. 1. The regulator assembly 120 may include a housing adapted to protect operational elements of the regulator assembly 120 from the ambient environment. As shown in FIG. 6A, the regulator assembly 120 may be similar to and operate as described above with respect to the regulator assembly 118 of FIG. 5C. In some embodiments, the regulator assembly 120 of FIG. 6A may include a regulator switch 800 and an electronic assembly 900.

The regulator switch 800 may be similar to and operate as described with respect to the regulator switch 600 of FIGS. 5A and 5B. Similar elements may have similar reference numbers indexed to 800. In some embodiments, the regulator switch 800 may include a housing 802 and a regulator valve 826. The housing 802 may have an end wall 803, one or more side walls 801, and an open end 805 opposite the end wall 803. The side walls 801 may be coupled to peripheral portions of and generally perpendicular to the end wall 803. In some embodiments, the electronic assembly 900 may be coupled to the side walls 801 of the regulator switch 800 proximate to the open end 805.

The housing 802 may be partitioned by a wall 804 to form a charging chamber 808 and a supply chamber 810. In some embodiments, the charging chamber 808 may adjoin the supply chamber 810, being disposed between the end wall 803, the wall 804, and the side walls 801. The supply chamber 810 may be disposed adjacent to the charging chamber 808. For example, in FIG. 6A, the wall 804 separates the charging chamber 808 and the supply chamber 810. The supply chamber 810 may be bounded by the wall 804, the side walls 801, and the electronic assembly 900. The wall 804 may be coupled to the side walls 801 of the housing 802 at peripheral portions of the wall 804. In some embodiments, no fluid communication may occur between the charging chamber 808, and the supply chamber 810 at the locations where the wall 804 couples to the housing 802.

The housing 802 and the wall 804 may be formed of a material having a sufficient strength to resist collapse if a negative pressure is supplied to the charging chamber 808 and the supply chamber 810, such as metals, hard plastics, or other suitable materials. For example, the housing 802 and the wall 804 may resist collapse if a negative pressure of about 150 mm Hg (−150 mm Hg gauge pressure) is supplied to the charging chamber 808 and the supply chamber 810. In other exemplary embodiments, the housing 802 and the wall 804 may resist collapse if a negative pressure of about 600 mm Hg (−600 mm Hg gauge pressure) is supplied to the charging chamber 808 and the supply chamber 810.

The charging chamber 808 may include a source port 814 and a charging port 816. The source port 814 may be disposed in one of the side walls 801 of the charging chamber 808 and may be fluidly coupled to the charging chamber 808. In some embodiments, the source port 814 may be configured to be fluidly coupled to a supply of negative pressure, such as an electric pump, a manual pump, or wall-suction source, for example. In some embodiments, the source port 814 may be fluidly coupled to a wall-suction source by a conduit or tube. A one-way valve may be disposed in the source port 814 and oriented to prevent fluid flow into the charging chamber 808 through the source port 814 and permit fluid flow out of the charging chamber 808 through the source port 814.

In some embodiments, the charging port 816 may be disposed in the wall 804, as shown in the illustrative embodiment of FIG. 6A. The charging port 816 may fluidly couple the charging chamber 808 and the supply chamber 810. In some embodiments, the charging port 816 may have a cylindrical wall 815 and a central passage 817 that extends between the charging chamber 808 and the supply chamber 810. The cylindrical wall 815 may include a portion extending into the supply chamber 810 from the wall 804. In some embodiments, the charging port 816 may be disposed in other locations of the wall 804. The charging port 816 may have a valve seat 824 on the distal end. The valve seat 824 may provide a tapered or beveled edge proximate to the central passage 817 of the charging port 816.

The supply chamber 810 may include a supply port 818. In some embodiments, the supply port 818 may be fluidly coupled to the supply chamber 810 and provide an interface to the supply chamber 810. For example, the supply port 818 may be configured to be coupled to a tube, which can be coupled to a dressing or other upstream component. A one-way valve may be disposed in the supply port 818 and oriented to permit fluid flow into the supply chamber 810 through the supply port 818 and prevent fluid flow out of the supply chamber 810 through the supply port 818.

In some embodiments, a fluid path may be provided between the charging port 816 and the supply chamber 810, which may be controlled by the regulator valve 826. The regulator valve 826 may include a valve member 822 and a regulator spring 834. The regulator valve 826 can be coupled to the side walls 801 and operably associated with the charging port 816 to regulate fluid communication between the charging chamber 808 and the supply chamber 810. The regulator valve 826 can be biased to either open or close the charging port 816. The regulator valve 826 may be coupled to ends of the side walls 801 of the housing 802, opposite the end wall 803 of the housing 802.

In some embodiments, the valve member 822 may be a flexible membrane, such as a diaphragm. The valve member 822 may have a generally disc-like shape. In other embodiments, the valve member 822 may have a shape matched to a shape of the regulator switch 800, for example, square, rectangular, ovoid, triangular, or amorphous shapes. The valve member 822 may have peripheral portions coupled to the side walls 801, and the valve member 822 may extend across the supply chamber 810. If the valve member 822 is coupled to the side walls 801, the valve member 822 may fluidly isolate the supply chamber 810 from the ambient environment surrounding the regulator switch 800. For example, a difference in the pressures in the supply chamber 810 and the ambient environment may cause deflection of the valve member 822. The valve member 822 may be formed from a silicone material. In some embodiments, the valve member 822 may have a hardness rating between about 80 Shore A and about 50 Shore A.

In some embodiments, the valve member 822 may include an enlarged portion 825 configured to engage the valve seat 824. The valve member 822 may be positioned so that the enlarged portion 825 of the valve member 822 may engage a beveled edge of the valve seat 824 of the charging port 816 in a closed position. If engaged in such a manner, the valve member 822 can substantially prevent fluid communication through the central passage 817 of the charging port 816.

The regulator spring 834 may be disposed on the charging port 816 so that the regulator spring 834 circumscribes the charging port 816. The regulator spring 834 may have a first end adjacent to the wall 804. In some embodiments, the first end of the regulator spring 834 may contact the wall 804 so that the regulator spring 834 may be compressed against the wall 804. A second end of the regulator spring 834 may be adjacent to the distal end of the charging port 816. The regulator spring 834 may have a length W if in a relaxed position. In the relaxed position, the regulator spring 834 may be longer than the charging port 816.

In some embodiments, the valve member 822 may include a conductor, such as a contact 848. The contact 848 may be positioned on a side of the valve member 822 facing away from the supply chamber 810. The contact 848 may have an electrically conductive periphery. In some embodiments, the contact 848 may be a resistor, such as a wire, a plate, or another device formed of an electrically conductive material, such as aluminum, copper, gold, or the like.

The electronic assembly 900 may be similar to the electronic assembly 700 of FIG. 5C. Similar elements may have similar reference numbers indexed to 900. The electronic assembly 900 may include a printed circuit board (PCB) 902, a first battery 906, a second battery 908, and a lighting assembly 910. The printed circuit board 902 may be an electronic device having one or more electronic components communicatively coupled by conductive pathways 903. In some embodiments, the printed circuit board 902 may include a power supply or electric potential source, such as the first battery 906 or the second battery 908, and a signal interface or indicator. The signal interface may be a visual device, such as a light emitting diode (LED) 912, an auditory device, such as a speaker or auditory pulse emitter, a tactile device, such as a moving protrusion, or an olfactory device. The printed circuit board 902 may further include an electronic storage device, such as a memory, a processing unit, and other devices.

In some embodiments, the regulator switch 800 may include an end wall coupled to the open end 805 of the regulator switch 800. In some embodiments, the PCB 902 may form the end wall of the regulator switch 800. The PCB 902 may be positioned over the end wall 803 and may be coupled to the side wall 801. The PCB 902 may include an opening 942 that may be proximate to a center of the PCB 902. In other embodiments, the opening 942 may not be proximate to the center of the PCB 902. In some embodiments, if the regulator switch 800 is coupled to the PCB 902, the opening 942 may be proximate to the enlarged portion 825 of the valve member 822.

In some embodiments, the PCB 902 may have a first electrical connector or a first terminal 944 and a second electrical connector or second terminal 946. The first terminal 944 and the second terminal 946 may be positioned on opposite sides of the opening 942. The first terminal 944 and the second terminal 946 may be electro-mechanical devices that allow joining of electrical circuits with a mechanical assembly, such as electrical connectors or terminals that connect two or more wires to a single connection point. In some embodiments, the first terminal 944 and the second terminal 946 may not be electrically coupled to each other across the opening 942. If the regulator switch 800 is coupled to the PCB 902, the contact 848 may be positioned proximate to the first terminal 944 and the second terminal 946. For example, the contact 848 may be positioned on a top of the valve member 822 so that deflection of the valve member 822 in response to a pressure differential across the valve member 822 may cause the contact 848 to physically touch the first terminal 944 and the second terminal 946. In some embodiments, the contact 848 may be positioned in a center of the valve member 822.

Figure 6B:
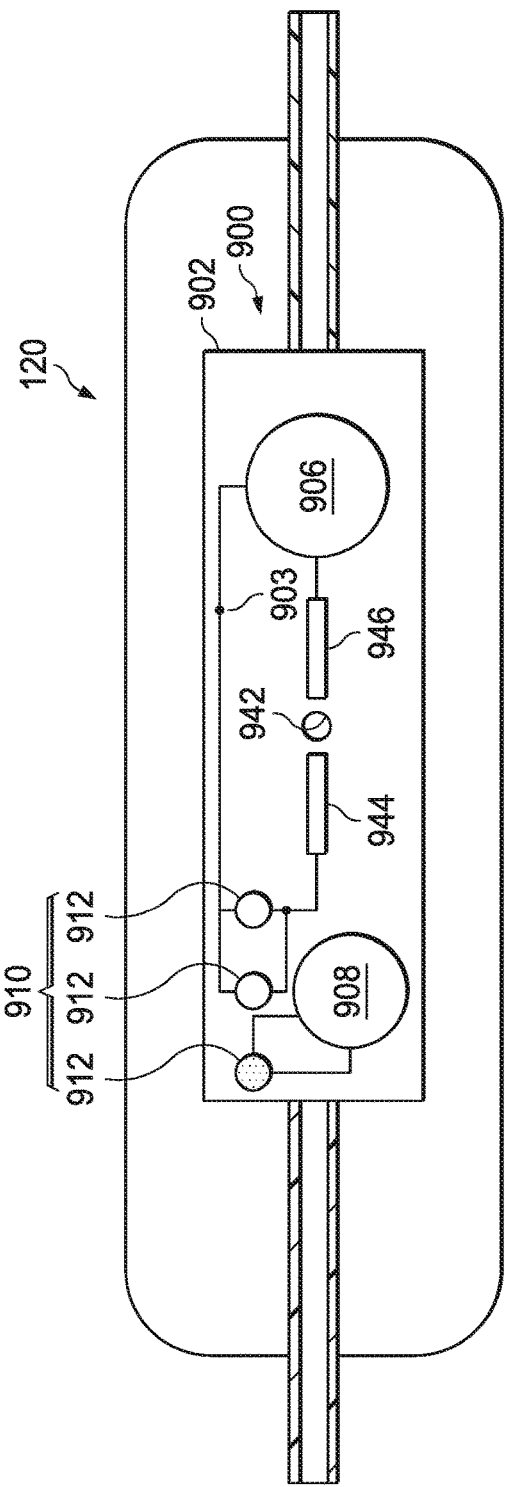
FIG. 6B is a schematic top view illustrating additional details that may be associated with the regulator assembly of FIG. 5A.

FIG. 6B is a schematic top view of the electronic assembly 900 illustrating additional details that may be associated with some embodiments. The first battery 906 and the second battery 908 may be further communicatively coupled to the LED 912 to provide current to the LED 912 for the operation thereof. In some embodiments, the first battery 906 may be electrically coupled to the second terminal 946 and further electrically coupled to one or more of the LEDs 912 of the lighting assembly 910. The LEDs 912 of the lighting assembly 910 that are electrically coupled to the first battery 906 may be further electrically coupled to the first terminal 944. If the contact 848 of the valve member 822 electrically couples the first terminal 944 and the second terminal 946, current may flow from the first battery 906 to the one or more LEDs 912 of the lighting assembly 910, illuminating the one or more LEDs 912. In some embodiments, the second battery 908 may be electrically coupled to at least one of the LEDs 912 of the lighting assembly 910. The second battery 908 may be in a closed circuit with the at least one LED 912 so that the second battery 908 provides a continuous current to the LED 912, maintaining the LED 912 in an illuminated state.

Referring to FIG. 6A, in some embodiments, a differential force may operate on the valve member 822. The differential force may be a force generated by a difference in pressures between the supply chamber 810 and the ambient environment of the regulator switch 800. The pressure in the supply chamber 810 may also be referred to as a supply pressure or the control pressure. If the supply pressure in the supply chamber 810 and the pressure in the ambient environment are substantially equal, the differential force may be approximately zero. If the supply pressure in the supply chamber 810 is less than the ambient pressure, for example, if the regulator switch 800 is being used to provide reduced-pressure therapy, the differential force may act to urge the valve member 822 toward the distal end of the charging port 816.

In some embodiments, the regulator spring 834 may exert a force in response to movement of the regulator spring 834 from the relaxed position. If the regulator spring 834 is disposed in the supply chamber 810, the regulator spring 834 may be moved from the relaxed position so that the regulator spring 834 has a length $W_1$. If the regulator spring 834 is compressed to the length $W_1$, the regulator spring 834 may exert a regulator force urging the valve member 822 away from the valve seat 824 of the charging port 816, and the contact 848 may be urged into electrical coupling with the first terminal 944 and the second terminal 946.

Generally, the regulator force exerted on the valve member 822 may be proportional to a distance the regulator spring 834 is moved from the relaxed position. Generally, the regulator spring 834 may be selected so that the differential force may overcome the regulator force if the supply pressure is about the therapy pressure. If the differential force overcomes the regulator force, the valve member 822 may contact the charging port 816 and prevent fluid communication through the charging port 816. In addition, the contact 848 may be moved out of the electrical coupling with the first terminal 944 and the second terminal 946.

If the differential force is greater than the force of the regulator spring 834 acting on the valve member 822, the valve member 822 may be urged into contact with the distal end of the charging port 816 to prevent fluid communication through the charging port 816 in a closed position. In response, the regulator spring 834 may be compressed to a length $W_2$. If the differential force is less than the force of the regulator spring 834, the valve member 822 may be urged away from the distal end of the charging port 816 to permit fluid communication through the charging port 816 in the open position, shown in FIG. 6A.

In some embodiments, the negative-pressure source 104 may be fluidly coupled to the source port 814, and the dressing 102 may be fluidly coupled to the supply port 818. In some embodiments, if the control pressure in the supply chamber 810 is about the ambient pressure, the valve member 822 may be urged out of contact with the distal end of the charging port 816, permitting fluid communication between the charging chamber 808 and the supply chamber 810. If the control pressure in the chamber 808 is about the ambient pressure, the contact 848 may be urged into electrical coupling with the first terminal 844 and the second terminal 846 by the regulator spring 834. In response, the one or more of the LEDs 912 of the lighting assembly 910 may be illuminated. In some embodiments, illumination of the one or more LEDs 912 that are electrically coupled to the first battery 906 may indicate that the pressure at the dressing 102 is not at the therapy pressure.

Operation of the negative-pressure source 104 may draw fluid from the dressing 102 through the supply port 818, the charging port 816, and the source port 814. As fluid is drawn from the supply chamber 810 through the charging port 816, the pressure may decrease in the supply chamber 810, increasing the differential force acting on the valve member 822. If the pressure in the supply chamber 810 is about the therapy pressure, the differential force may urge the valve member 822 into contact with the valve seat 824 of the charging port 816, blocking the charging port 816 and stopping the supply of negative pressure to the dressing 102. In addition, the contact 848 may be moved out of the electrical coupling with the first terminal 944 and the second terminal 946, stopping the flow of current to the LEDs 912 of the lighting assembly 910. In response, the LEDs 912 may no longer be illuminated, providing a visual indication that the pressure at the dressing 102 may be about the therapy pressure.

If the first terminal 844 and the second terminal 846 are not electrically coupled, electric current may not flow to the lighting assembly 910. In response to the flow of electric current through the first terminal 844 and the second terminal 846, the lighting assembly 910 may light one or more of the LEDs 912 to provide an indication of the state of operation of the negative-pressure source 104.

Figure 7:
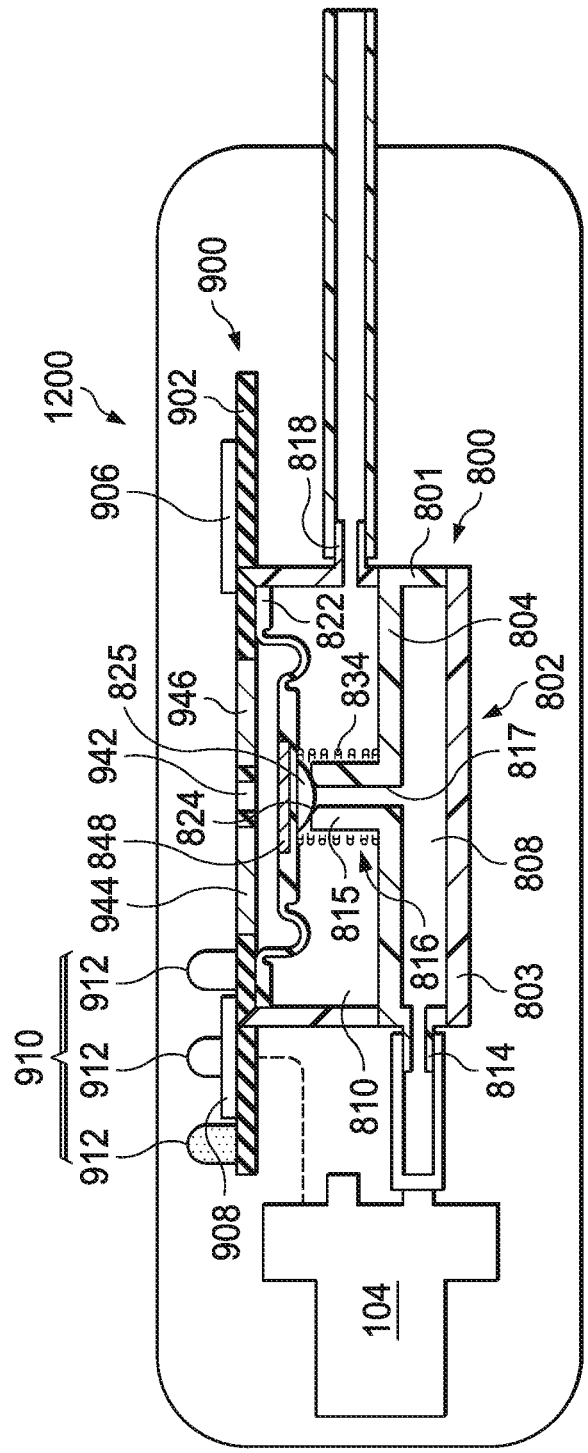
FIG. 7 is a schematic diagram illustrating additional details that may be associated with another embodiment of the regulator switch of FIG. 5A disposed in a negative-pressure assembly.

FIG. 7 is a schematic illustration of a negative-pressure assembly 1200 that may be used with some embodiments of the therapy system 100 of FIG. 1. The negative-pressure assembly 1200 may include a housing adapted to protect operational elements of negative-pressure assembly 1200 from the ambient environment. As shown in FIG. 7, the negative-pressure assembly 1200 may include the negative-pressure source 104, the regulator switch 800, and the electronic assembly 900. The negative-pressure source 104 may be electrically coupled to the PCB 902 and fluidly coupled to the source port 814 to provide a self-contained source and regulation unit. In some embodiments, the negative-pressure source 104 may be electrically coupled to the first battery 906 through the PCB 902. If the pressure in the supply chamber 810 is about the ambient pressure, the regulator force may be stronger than the differential force so that the valve member 822 is urged into contact with the PCB 902, and the contact 848 is electrically coupled to the first terminal 944 and the second terminal 946. In response, current may flow from the first battery 906 to the negative-pressure source 104. In response to the current, the negative-pressure source 104 may operate to draw fluid from the dressing 102 through the supply port 818, the charging port 816, and the source port 814. As fluid is drawn from the supply chamber 810, the pressure in the supply chamber 810 may approach the therapy pressure. If the pressure in the supply chamber 810 is about the therapy pressure, the differential force may overcome the regulator force, and the valve member 822 may be urged into contact with the valve seat 824 of the charging port 816, stopping fluid flow through the charging port 816. In addition, the contact 848 may be taken out of the electrical coupling with the first terminal 944 and the second terminal 946, stopping the flow of current to the negative-pressure source 104. In response, the negative-pressure source 104 may stop operating.

If the pressure in the supply chamber 810 moves toward ambient pressure, the regulator force may again overcome the differential force, urging the valve member 822 into contact with the PCB 902 and electrically coupling the contact 848 with the first terminal 944 and the second terminal 946. In response, current may flow to the negative-pressure source 104 from the first battery 906, causing the negative-pressure source 104 to operate.

Figure 8:
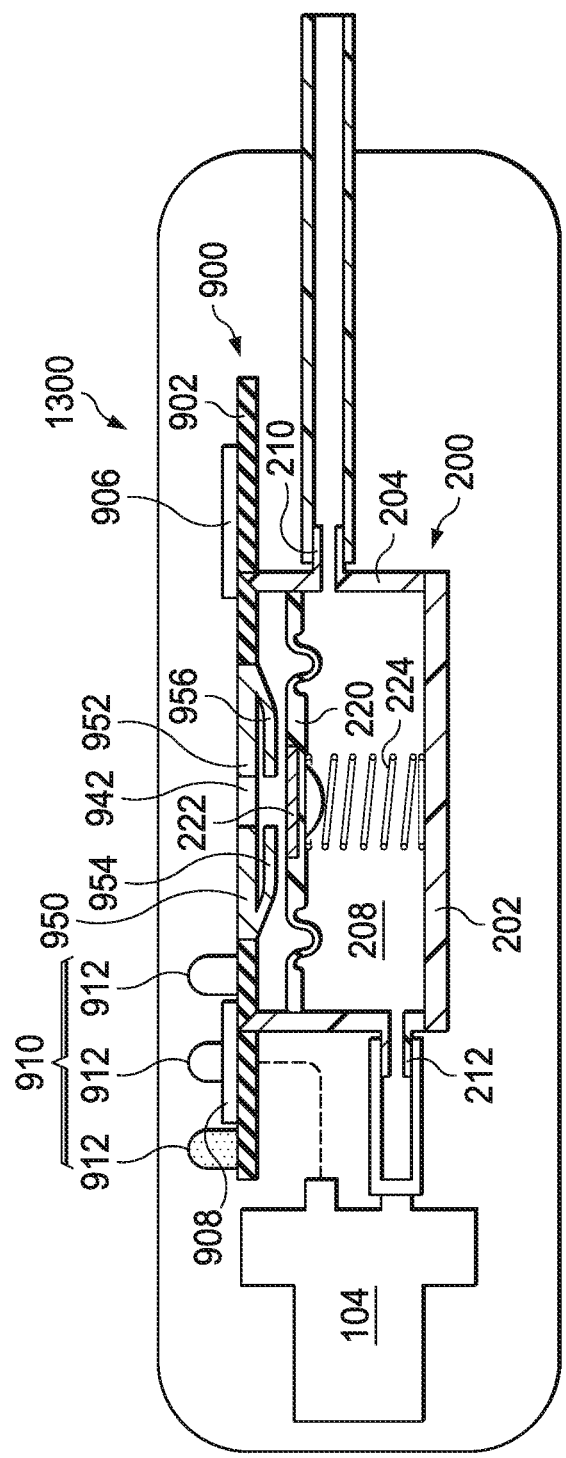
FIG. 8 is a schematic diagram illustrating additional details that may be associated with another embodiment of the switch of FIG. 2A disposed in a negative-pressure therapy assembly.

FIG. 8 is a schematic illustration of a negative-pressure assembly 1300 that may be used with some embodiments of the therapy system 100 of FIG. 1. The negative-pressure assembly 1300 may include a housing adapted to protect operational elements of negative-pressure assembly 1300 from the ambient environment. As shown in FIG. 8, the negative-pressure assembly 1300 may include the negative-pressure source 104, the switch 200, and the electronic assembly 900. The negative-pressure source 104 may be electrically coupled to the PCB 902 and fluidly coupled to the fluid outlet 212.

The switch 200 may include an end wall 202 and one or more side walls 204. In some embodiments, the end wall 202 may be circular. The side wall 204 may be a tubular wall and have a first end coupled to a periphery of the end wall 202. In some embodiments, the side wall 204 may have a length extending away from the end wall 202. The electronic assembly 900 may be coupled to the side wall 204 opposite the end wall 202. The end wall 202, the electronic assembly 900, and the side wall 204 may be collectively referred to as a housing. In some embodiments, the end wall 202, the electronic assembly 900, and the side wall 204 may form a chamber 208. In some embodiments, the chamber 208 may be fluidly isolated from the ambient environment.

In some embodiments, the switch 200 may further include a fluid inlet 210 and the fluid outlet 212. The fluid inlet 210 may be coupled to the side wall 204. The fluid inlet 210 may provide a path for fluid communication between the ambient environment and the chamber 208. In some embodiments, the fluid inlet 210 may be coupled to a tube or other mechanism so that the chamber 208 may be in fluid communication with another device, such as the dressing 102, through the fluid inlet 210.

In some embodiments, the fluid outlet 212 may be coupled to the side wall 204. The fluid outlet 212 may be positioned on an opposite side of the switch 200 from the fluid inlet 210. In other embodiments, the fluid inlet 210 and the fluid outlet 212 may be proximate to one another. The fluid outlet 212 may provide a path for fluid communication between the ambient environment and the chamber 208. In some embodiments, the fluid outlet 212 may be coupled to a tube or other mechanism so that the chamber 208 may be in fluid communication with another device, such as the negative-pressure source 104, through the fluid outlet 212.

In some embodiments, the PCB 902 may include an opening 942. The opening 942 may be proximate to a center of the PCB 902. In other embodiments, the opening 942 may not be proximate to the center of the PCB 902. In some embodiments, the opening 942 may permit fluid communication through the PCB 902 with the chamber 208.

In some embodiments, an actuator, such as a flexible membrane or a diaphragm 220, may be disposed in the chamber 208. The diaphragm 220 may be positioned proximate to the end wall 206. The diaphragm 220 may have peripheral portions coupled to the side wall 204, and the diaphragm 220 may extend across the chamber 208. If the diaphragm 220 is coupled to the side wall 204, the diaphragm 220 may fluidly isolate the chamber 208 from the ambient environment. For example, a difference in the pressures in the chamber 208 and the ambient environment may cause deflection of the diaphragm 220. In some embodiments, the diaphragm 220 may be a disc with a diameter larger than the diameter of the opening 942 in the PCB 902. In other embodiments, the diaphragm 220 may have other shapes configured to fluidly isolate the opening 942 from the chamber 208. In some embodiments, the diaphragm 220 may be formed from a silicone material, and the diaphragm 220 may have a hardness rating between about 30 Shore A and about 50 Shore A.

In some embodiments, the diaphragm 220 may include a conductor, such as a contact 222. The contact 222 may be positioned on a side of the diaphragm 220 facing the PCB 902. The contact 222 may be positioned proximate to a first terminal 950 and a second terminal 952. For example, the contact 222 may be positioned on a top of the diaphragm 220 so that deflection of the diaphragm 220 in response to a pressure differential across the diaphragm 220 may cause the contact 222 to physically touch the first terminal 950 and the second terminal 952. In some embodiments, the contact 222 may be positioned in a center of the diaphragm 220 and have a width that permits the contact 222 to straddle the opening 942. The contact 222 may have an electrically conductive periphery. In some embodiments, the contact 222 may be a resistor, such as a wire, a plate, or another device formed of an electrically conductive material, such as aluminum, copper, gold, or the like. In some embodiments, the contact 222 may be an integral member of the diaphragm 220. For example, the diaphragm 220 may be formed of a conductive material, may be coated in a conductive material, or may be doped in a conductive material.

In some embodiments, the actuator may be biased. For example, the actuator may have elastic properties biasing the actuator to a particular position. For example, the actuator may be formed of a thin metal, elastomer, rubber, or other elastically deformable material, which may be deformed in response to a pressure differential and return to its natural position if the pressure differential is removed. The actuator may also include a biasing member, such as a spring 224, disposed in the chamber 208. The spring 224 may have a first end proximate to the end wall 202 and a second end operatively coupled to the diaphragm 220. In some embodiments, the first end of the spring 224 may be coupled to the end wall 202. The spring 224 may be compressed between the end wall 202 and the diaphragm 220. In some embodiments, the spring 224 may have a length X in a relaxed position. In the relaxed position, the spring 224 may be neither extended nor compressed so that spring 224 does not exert a spring force. In some embodiments, the spring 224 may have a length $X_1$ in a slightly compressed position. If the spring 224 is in the slightly compressed position, the spring 224 may exert a force on the diaphragm 220, urging the diaphragm 220 into contact with the PCB 902 and the contact 222 into an electrical coupling with the first terminal 950 and the second terminal 952.

A differential force may also operate on the diaphragm 220. The differential force may be a force generated by a difference in pressures between the chamber 208 and the ambient environment of the switch 200. The pressure in the chamber 208 may also be referred to as a control pressure. If the control pressure in the chamber 208 and the pressure in the ambient environment are substantially equal, the differential force may be approximately zero. If the control pressure in the chamber 208 is less than the ambient pressure, for example, if the switch 200 is being used to provide reduced-pressure therapy, the differential force may act to urge the diaphragm 220 away from the electronic assembly 900. If the differential force is less than the force of the spring 224 acting on the diaphragm 220, the diaphragm 220 may be urged into contact with the electronic assembly 900. If the differential force is greater than the spring force, the diaphragm 220 may compress the spring 224 against the end wall 202.

The electronic assembly 900 may be similar to the electronic assembly 900 of FIG. 6A and FIG. 6B. The electronic assembly 900 may include the printed circuit board (PCB) 902, the first battery 906, the second battery 908, and the lighting assembly 910. The printed circuit board 902 may be an electronic device having one or more electronic components communicatively coupled by conductive pathways. In some embodiments, the printed circuit board 902 may include a power supply or electric potential source, such as the first battery 906 or the second battery 908, and a signal interface or indicator. In some embodiments, the signal interface may be a visual device, such as the light emitting diode (LED) 912, an auditory device, such as a speaker or auditory pulse emitter, a tactile device, such as a moving protrusion, or an olfactory device. The printed circuit board 902 may further include an electronic storage device, such as a memory, a processing unit, and other devices.

In some embodiments, the PCB 902 may form an end wall of the switch 200 as described above. The PCB 902 may be positioned over the end wall 202 and may be coupled to the side wall 204. The PCB 902 may include the opening 942. In some embodiments, the opening 942 may be proximate to a center of the PCB 902. In other embodiments, the opening 942 may not be proximate to the center of the PCB 902. In some embodiments, if the switch 200 is coupled to the PCB 902, the opening 942 may be proximate to the contact 222 of the diaphragm 220.

In some embodiments, the printed circuit board (PCB) 902 may include a first terminal 950 and the second terminal 952. The first terminal 950 and the second terminal 952 may be positioned on the PCB 902 similar to the first terminal 944 and the second terminal 946. The first terminal 950 and the second terminal 952 may be electro-mechanical devices that allow joining of electrical circuits with a mechanical assembly, such as electrical connectors or terminals that connect two or more wires to a single connection point. In some embodiments, the first terminal 950 and the second terminal 952 may not be electrically coupled to each other through the PCB 902.

In some embodiments, the first terminal 950 and the second terminal 952 may include biasing elements, such as a first spring 954 and a second spring 956. The first spring 954 may be coupled to the first terminal 950 and be positioned between the first terminal 950 and the diaphragm 220. Similarly, the second spring 956 may be coupled to the second terminal 952 and be positioned between the second terminal 952 and the diaphragm 220. In some embodiments, the first spring 954 and the second spring 956 may be cantilevered springs having an end fixed to the first terminal 950 and the second terminal 952, respectively. The first spring 954 and the second spring 956 may extend from the fixed end toward the diaphragm 220 at an angle to the PCB 902. The first spring 954 and the second spring 956 may also have a free end opposite the fixed end that is configured to contact the contact 222 of the diaphragm 220. In some embodiments, the first spring 954 and the second spring 956 may be electrically conductive, and the first spring 954 and the second spring 956 may extend the period of contact between the contact 222, the first terminal 950, and the second terminal 952.

The first battery 906 and the second battery 908 may be further communicatively coupled to the LEDs 912 to provide current to the LEDs 912 for the operation thereof. In some embodiments, the first battery 906 may be electrically coupled to the second terminal 946 and further electrically coupled to one or more of the LEDs 912 of the lighting assembly 910. The LEDs 912 of the lighting assembly 910 that are electrically coupled to the first battery 906 may be further electrically coupled to the first terminal 944. If the contact 222 of the diaphragm 220 electrically couples the first terminal 944 and the second terminal 946, current may flow from the first battery 906 to the one or more LEDs 912 of the lighting assembly 910, illuminating the one or more LEDs 912. In some embodiments, the second battery 908 may be electrically coupled to at least one of the LEDs 912 of the lighting assembly 910. The second battery 908 may be in a closed circuit with the at least one LED 912 so that the second battery 908 provides a continuous current to the LED 912, maintaining the LED 912 in an illuminated state.

In some embodiments, the switch 200 may be fluidly coupled to the negative-pressure source 104. For example, the negative-pressure source 104 may be fluidly coupled to the fluid outlet 212, and the dressing 102 may be fluidly coupled to the fluid inlet 210. In some embodiments, the negative-pressure source 104 may be operatively coupled to the PCB 902 and the first battery 906 for operation of the negative-pressure source 104. In some embodiments, an electric circuit coupling the negative-pressure source 104 to the first battery 906 may include the first terminal 950 and the second terminal 952. For example, electric current may flow from the first battery 906 to the second terminal 952, and electric current may flow from the first terminal 950 to the negative-pressure source 104. If the first terminal 950 and the second terminal 952 are electrically coupled, such as through the contact 222, then electric current may flow from the first battery 906 to the negative-pressure source 104, powering the negative-pressure source 104 for operation. If the first terminal 950 and the second terminal 952 are not electrically coupled, electric current may not flow from the first battery 906 to the negative-pressure source 104, and the negative-pressure source 104 may not operate.

In some embodiments, if the control pressure is about equal to the ambient pressure, the contact 222 may be urged into an electrical coupling with the first terminal 950 and the second terminal 952 by the spring 224. For example, without a pressure differential across the diaphragm 220, the spring 224 can press the contact 222 against the first terminal 950 and the second terminal 952. In response, an electric current may flow between the first terminal 950 and the second terminal 952 through the contact 222. In some embodiments, the negative-pressure source 104 may receive the electric current, and the electric current may power a pump of the negative-pressure source 104 to draw fluid from the dressing 102 through the fluid inlet 210 and the fluid outlet 212. As fluid is drawn from the chamber 208 through the fluid outlet 212, the pressure in the chamber 208 may decrease and approach the therapy pressure. Decreasing the pressure in the chamber 208 may increase the differential force. In some embodiments, if the pressure in the chamber 208 is about the therapy pressure, the differential force may overcome the force of the spring 224, moving the diaphragm 220 away from the PCB 902 and breaking the electrical coupling between the first terminal 950 and the second terminal 952 through the contact 222. In response, the electric current may no longer flow between the first terminal 950 and the second terminal 952. If the negative-pressure source 104 is electrically coupled to the first battery 906 through the switch 200, stopping the flow of electric current removes the source of power from the pump of the negative-pressure source 104, stopping the operation of the negative-pressure source 104.

If the pressure in the chamber 208 increases, that is, moves toward the ambient pressure from the therapy pressure, the spring 224 may overcome the differential force, urging the diaphragm 220 into contact with the PCB 902. In response, the electrical connection between the negative-pressure source 104 and the first battery 906 may be reestablished and electric current may flow between the first terminal 950 and the second terminal 952 through the contact 222, allowing the negative-pressure source 104 to operate and draw fluid from the chamber 208 through the fluid outlet 212.

The first spring 954 and the second spring 956 of the first terminal 950 and the second terminal 952 increase the length of time that the contact 222 is electrically coupled to the electronic assembly 900. In response, the negative-pressure source 104 may be operated longer, allowing for greater confidence that the therapy pressure at the dressing 102 has been reached.

Figure 9:
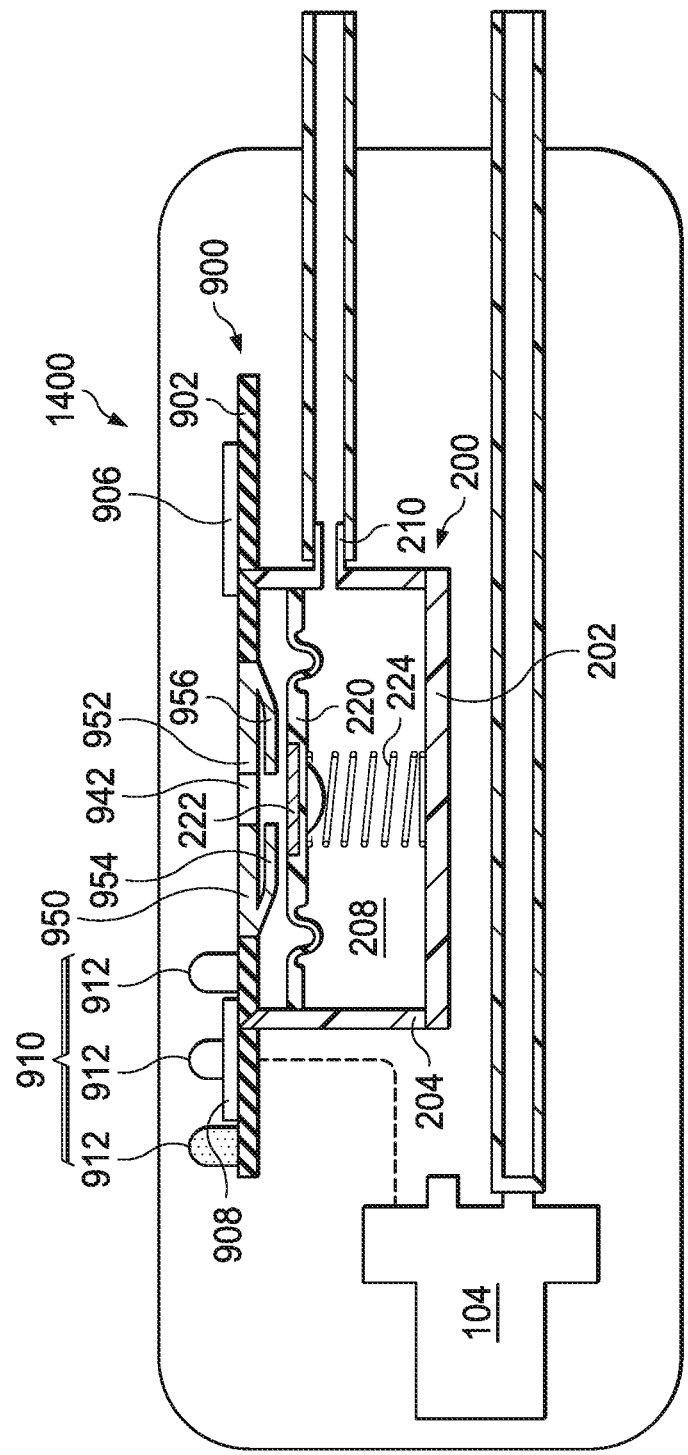
FIG. 9 is a schematic diagram illustrating additional details that may be associated with another embodiment of the switch of FIG. 2A disposed in a negative-pressure assembly.

FIG. 9 is a sectional schematic view illustrating a negative-pressure assembly 1400 that may be used with some embodiments of the therapy system 100 of FIG. 1. The negative-pressure assembly 1400 of FIG. 9 may be similar to and operate as described above with respect to the negative-pressure assembly 1300 of FIG. 8. Similar elements may include similar reference numbers and operate as described above with respect to FIGS. 2A, 2B, and 8. As shown in FIG. 9, the switch 200 may have the fluid outlet 212 removed. In response, the negative-pressure source 104 may be directly coupled to the dressing 102. The fluid inlet 210 may also be directly coupled to the dressing 102. In the exemplary embodiment of FIG. 9, the switch 200 may operate as a feedback mechanism. The pressure at the dressing 102 may be communicated to the chamber 208 of the switch 200. In response, the differential force may act on the diaphragm 220 to control the operation of the components on the PCB 902 and the negative-pressure source 104. As current flows or does not flow between the first terminal 950 and the second terminal 952 through the contact 222, the negative-pressure source 104 may be operated or stopped in response.

Figure 10:
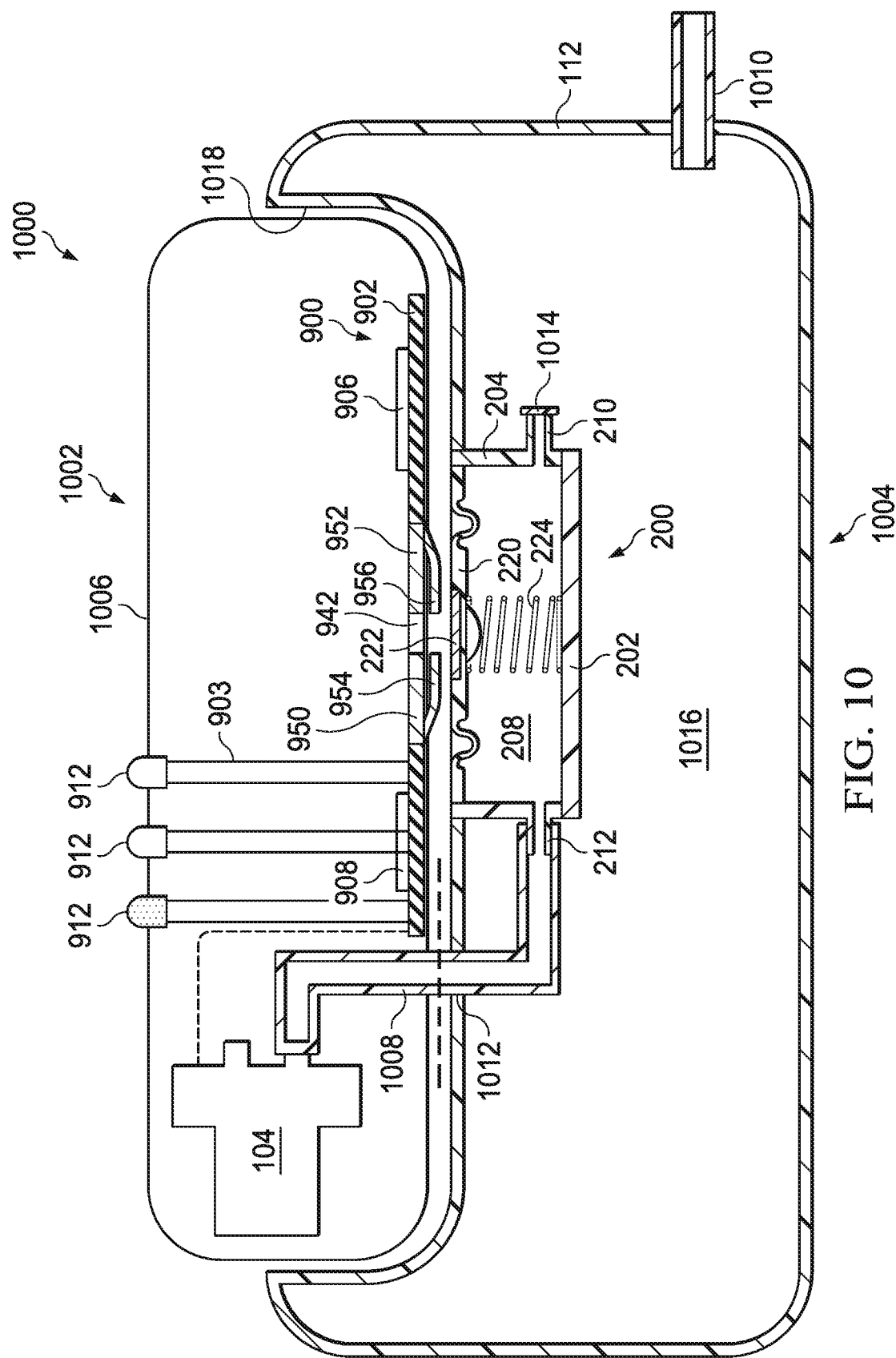
FIG. 10 is a schematic diagram illustrating additional details that may be associated with another embodiment of the switch of FIG. 2A disposed in a negative-pressure assembly.

FIG. 10 is a schematic illustration of a negative-pressure assembly 1000 having a combination negative-pressure source, switch, and container that may be used with some embodiments of the therapy system 100 of FIG. 1. The negative-pressure assembly 1000 may include a control unit 1002 housing the negative-pressure source 104 and the electronic assembly 900 and a container 1004 housing the container 112 and the switch 200.

The control unit 1002 may include a housing 1006. The housing 1006 may be a container configured to provide a mounting location for the negative-pressure source 104 and the electronic assembly 900. In some embodiments, the housing 1006 may be configured to protect the negative-pressure source 104 and the electronic assembly 900 from the ambient environment. The housing 1006 may include a fluid inlet port 1008. The fluid inlet port 1008 may be fluidly coupled to the negative-pressure source 104 and provide a connection for fluid communication between the negative-pressure source 104 and an exterior of the housing 1006. In some embodiments, the fluid inlet port 1008 may be fluidly coupled to a dressing, such as the dressing 102 or a container, such as the container 1004.

The electronic assembly 900 may be disposed in an interior of the housing 1006 and may include the components of the electronic assembly 900 and operate as described above with respect to FIG. 8 and FIG. 9. The PCB 902 may be coupled to the housing 1006 so that at the least the first spring 954 of the first terminal 950 and the second spring 956 of the second terminal 952 may be exposed to the ambient environment. In some embodiments, the first spring 954 and the second spring 956 may be positioned proximate to the fluid inlet port 1008. In some embodiments, the light assembly 910 may be coupled to the housing 1006 so that one or more of the LEDs 912 may be exposed to the ambient environment. In some embodiments, one or more of the LEDs 912 may be visible from an exterior of the housing 1006.

The negative-pressure assembly 1000 may also include the container 1004. The container 1004 may house the switch 200 and the container 112. The container 112 may be a fluid container having a fluid chamber 1016, a fluid inlet port 1010, and a fluid outlet port 1012. In some embodiments, the fluid inlet port 1010 may be fluidly coupled to the fluid chamber 1016 and may be adapted to be fluidly coupled to a dressing, such as the dressing 102. The fluid outlet port 1012 may be exposed on an exterior of the container 1004 so that the fluid outlet port 1012 may be fluidly coupled to the fluid inlet port 1008 of the control unit 1002.

The switch 200 may be disposed in the fluid chamber 1016. The switch 200 may be fluidly isolated from fluid in the fluid chamber 1016. In some embodiments, the switch 200 may be positioned in the container 1004 so that the diaphragm 220 and the contact 222 may be accessible from an exterior of the container 1004. In some embodiments, the fluid inlet 210 may be fluidly coupled to the fluid chamber 1016 so that fluid may flow from the fluid chamber 1016 into the chamber 208. In some embodiments, the fluid inlet 210 may have a filter 1014 coupled to the fluid inlet 210. The filter 1014 may prevent communication of liquid from the fluid chamber 1016 into the chamber 208 of the switch 200. The fluid outlet 212 may be fluidly coupled to the fluid outlet port 1012.

In some embodiments, the container 1004 may be shaped to receive the control unit 1002. For example, the container 1004 may include a cavity 1018. The cavity 1018 may be sized and shaped to receive the control unit 1002. In some embodiments, the diaphragm 220 and the contact 222 of the switch 200 and the fluid outlet port 1012 may be positioned on a same surface in the cavity 1018. The fluid inlet port 1008, the first spring 954 and the second spring 956 may be positioned on a same surface of the control unit 1002. If the control unit 1002 is coupled to the container 1004, the control unit 1002 may be positioned within the cavity 1018. If the control unit 1002 is positioned within the cavity 1018, the first spring 954 and the second spring 956 may be proximate to the contact 222, and the fluid inlet port 1008 may be fluidly coupled to the fluid outlet port 1012.

Figure 11:
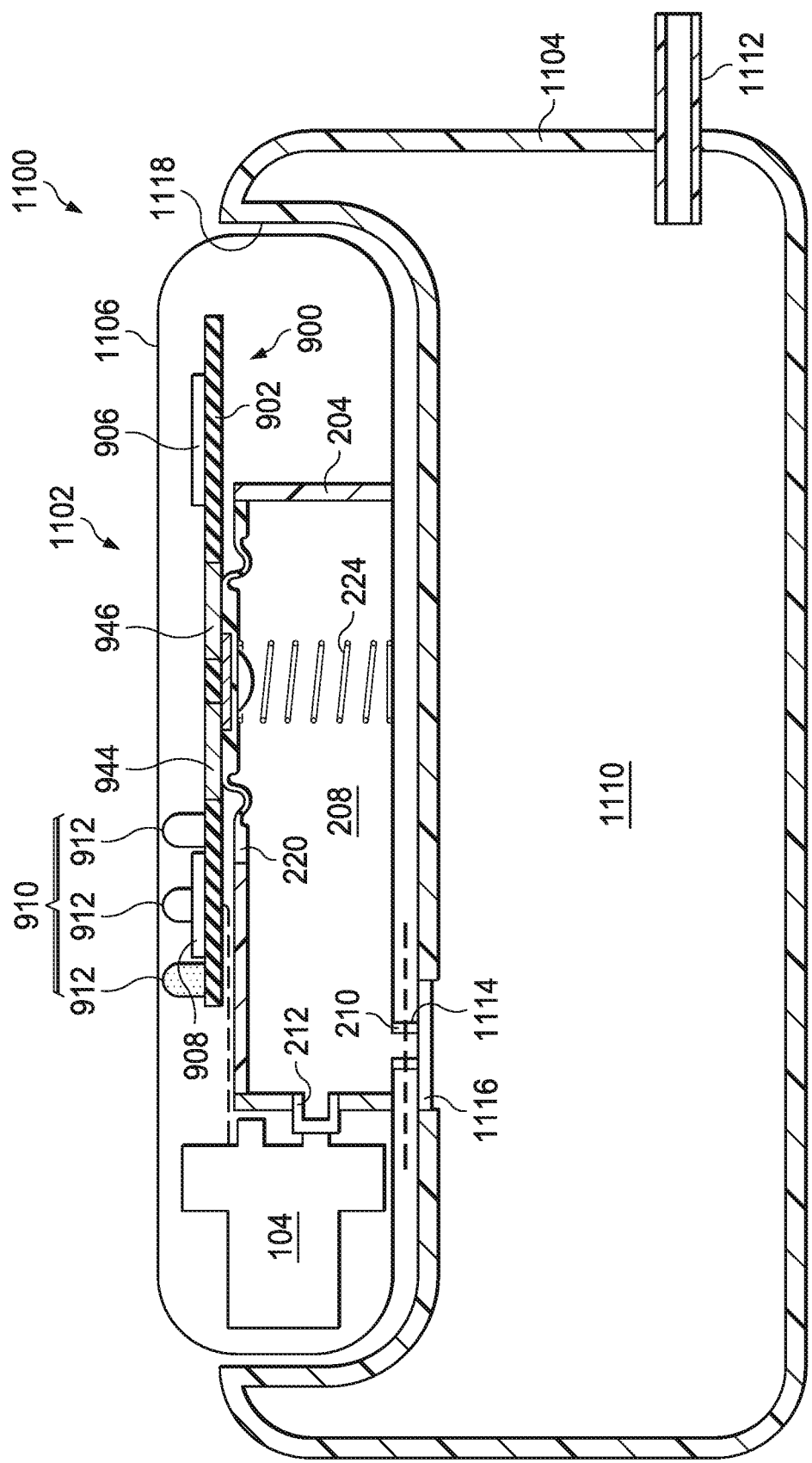
FIG. 11 is a schematic diagram illustrating additional details that may be associated with another embodiment of the switch of FIG. 2A disposed in a negative-pressure assembly.

FIG. 11 is a schematic illustration of a negative-pressure assembly 1100 having a combination negative-pressure source, switch, and container that may be used with some embodiments of the therapy system 100 of FIG. 1. The negative-pressure assembly 1100 may include a control unit 1102 housing the negative-pressure source 104, the switch 200, and the electronic assembly 900 and a container 1104.

The control unit 1102 may include a housing 1106. The housing 1106 may be a container configured to provide a mounting location for the negative-pressure source 104, the switch 200, and the electronic assembly 900. In some embodiments, the housing 1106 may be configured to protect the negative-pressure source 104, the switch 200, and the electronic assembly 900 from the ambient environment.

The switch 200 may be similar to and operate as described with respect to the switch 200 of FIG. 8 and FIG. 9. In some embodiments, the switch 200 may be disposed in the housing 1106. The fluid inlet 210 may be exposed on an exterior of the housing 1106. The fluid inlet 210 may permit a fluid connection between an upstream device and the control unit 1102. The fluid outlet 212 of the switch 200 may be fluidly coupled to the negative-pressure source 104. The electronic assembly 900 may be similar to and operate as described with respect to the electronic assembly 900 of FIG. 8 and FIG. 9. In some embodiments, the PCB 902 may be coupled to the housing 1106 so that the first terminal 950 and the second terminal 952 may be proximate to the diaphragm 220 and the contact 222. In some embodiments, the light assembly 910 may be coupled to the housing 1006 so that one or more of the LEDs 912 may be visible from an exterior of the housing 1106 during the operation of the negative-pressure assembly 1100.

The negative-pressure assembly 1100 may also include the container 1104. The container 1104 may be a fluid container similar to the container 1004 of FIG. 10 and the container 112 of FIG. 1. In some embodiments, the container 1104 may have a cavity 1118 formed on an exterior of the container 1104. The cavity 1118 may be sized and shape to receive the control unit 1102. In some embodiments, the container 1104 may include a fluid chamber 1110, a fluid inlet port 1112, and a fluid outlet port 1114. The fluid inlet port 1112 may be fluidly coupled to the fluid chamber 1110 and may be adapted to be fluidly coupled to a dressing, such as the dressing 102. The fluid outlet port 1114 may also be fluidly coupled to the fluid chamber 1110. In some embodiments, the fluid outlet port 1114 may be positioned on an exterior of the container 1104. For example, the fluid outlet port 1114 may be positioned on a surface of the cavity 1118. The fluid outlet port 1114 may provide a fluid connection between the fluid chamber 1110 and the control unit 1102. In some embodiments, the fluid outlet port 1114 may have a filter 1116 coupled to the fluid outlet port 1114. The filter 1116 may be configured to permit fluid flow through the filter 1116 but block liquid from leaving the fluid chamber 1110 through the fluid outlet port 1114. In some embodiments, the filter 1116 may be hydrophobic.

The systems, apparatuses, and methods described herein may provide significant advantages. For example, some embodiments of the pressure switches can be used to provide feedback in systems with externally controlled vacuum sources. Some systems may have a negative-pressure source that is integrated but not directly controlled by a pressure switch. Yet other embodiments can use a pressure switch to directly control a negative-pressure source. The pressure switches described herein can also significantly reduce the part count and manufacturing cost for a system that provides negative-pressure therapy, while maintaining the same or similar performance and function. The systems described herein may also be simpler than other comparable systems for providing negative-pressure therapy and accomplish this without a loss of functional features. Additionally, the pressure switches described herein may not be considered waste under the Waste Electrical and Electronic Equipment Directive (WEEE), and can be disposed of without the power supply. Increased flow rates, increased fluid management, and increased customization can also be achieved.

While shown in a few illustrative embodiments, a person having ordinary skill in the art will recognize that the systems, apparatuses, and methods described herein are susceptible to various changes and modifications. For example, a regulator may be placed in a control unit as shown in FIG. 11, or may be placed in a disposable portion of a therapy system, such as a canister, and provide an electrical connection back to a pump and batteries as shown in FIG. 10, which may be in a smaller and simpler therapy unit that can be re-used. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for providing negative pressure therapy, the system comprising:
 a negative-pressure source;
 an energy source; and
 a switch comprising:
  a housing forming a chamber and having a fluid inlet, a fluid outlet and an ambient pressure opening;
  a first conductor electrically coupled to the negative-pressure source;
  a second conductor electrically coupled to the energy source, the first conductor and the second conductor being positioned on opposite sides of the ambient pressure opening; and
  a diaphragm having a first position electrically coupling the first conductor to the second conductor and a second position separated from the first conductor and the second conductor, the diaphragm configured to move between the first position and the second position in response to a differential between a control pressure and a therapy pressure.

2. The system of claim 1, wherein the switch further comprises:
 a biasing member disposed in the chamber and having a first end coupled to the diaphragm and a second end coupled to the housing; and
 the diaphragm fluidly isolates the chamber from the ambient pressure opening.

3. The system of claim 2, wherein the diaphragm is coupled to the housing over the ambient pressure opening and the biasing member is configured to bias the diaphragm to the second position.

4. The system of claim 3, wherein the switch further comprises:
a calibration spring having a first end operatively coupled to the diaphragm; and
a calibrator coupled to a second end of the calibration spring, the calibrator operable to calibrate a differential force required to move the diaphragm from the second position to the first position.

5. The system of claim 1, further comprising:
a printed circuit board;
a controller coupled to the printed circuit board;
at least one light emitting diode coupled to the printed circuit board and electrically coupled to the controller; and
wherein the first conductor and the second conductor are electrically coupled to the controller and the controller is configured to operate the at least one light emitting diode in response to the diaphragm being in at least one of the first position and the second position.

6. The system of claim 1, further comprising a regulator fluidly coupled to the negative-pressure source and the switch, the regulator comprising:
a supply chamber adapted to be fluidly coupled to a dressing;
a charging chamber fluidly coupled to the supply chamber through a port; and
a regulator valve coupled to the charging chamber and operable to reciprocate to control fluid communication through the port based on a differential between an ambient pressure and a therapy pressure.

7. The system of claim 1, wherein the switch further comprises:
a supply chamber adapted to be fluidly coupled to a dressing;
a charging chamber fluidly coupled to the supply chamber through a port; and
the diaphragm coupled to the charging chamber and operable to reciprocate to control fluid communication through the port based on a differential between an ambient pressure and a therapy pressure.

8. A pressure-actuated switch for operation by a negative-pressure system, the switch comprising:
a housing forming a chamber and having a fluid inlet, a fluid outlet and an ambient pressure opening;
a first terminal electrically coupled to a negative-pressure source;
a second terminal electrically coupled to an energy source, the first terminal and the second terminal being positioned on opposite sides of the ambient pressure opening; and
a membrane configured to conduct electricity disposed proximate to the first terminal and the second terminal, the membrane having a first position electrically coupling the first terminal to the second terminal and a second position separated from the first terminal and the second terminal, the membrane configured to move between the first position and the second position in response to a differential between an ambient pressure and a therapy pressure.

9. The switch of claim 8, further comprising a third terminal disposed on the membrane and proximate to the first terminal and the second terminal.

10. The switch of claim 8, wherein the switch further comprises:
a spring disposed in the chamber and having a first end coupled to the membrane and a second end coupled to the housing; and
the membrane disposed in the chamber and coupled to the housing proximate to the ambient pressure opening to fluidly isolate the chamber from an ambient environment.

11. The switch of claim 10, wherein the membrane is disposed in the chamber and the spring is configured to bias the membrane to the first position.

12. The switch of claim 11, wherein the switch further comprises a calibrator coupled to the second end of the spring and operable to calibrate a differential force required to move the membrane from the first position to the second position.

13. The switch of claim 10, wherein the membrane is coupled to the housing over the ambient pressure opening and the spring is configured to bias the membrane to the second position.

14. The switch of claim 13, wherein the switch further comprises:
a calibration spring having a first end operatively coupled to the membrane; and
a calibrator coupled to a second end of the calibration spring, the calibrator operable to calibrate a differential force required to move the membrane from the second position to the first position.

15. The switch of claim 8, further comprising:
a printed circuit board;
a controller coupled to the printed circuit board;
at least one light emitting diode coupled to the printed circuit board and electrically coupled to the controller; and
wherein the first terminal and the second terminal are electrically coupled to the controller and the controller is configured to operate the at least one light emitting diode in response to the membrane being in at least one of the first position and the second position.

16. The switch of claim 8, wherein the switch further comprises:
a supply chamber adapted to be fluidly coupled to a dressing;
a charging chamber fluidly coupled to the supply chamber through a port; and
the membrane coupled to the charging chamber and operable to reciprocate to control fluid communication through the port based on a differential between an ambient pressure and a therapy pressure.

17. The switch of claim 8, wherein the first terminal and the second terminal are sprung terminals.

18. A method for regulating negative-pressure therapy comprising:
providing a negative-pressure source;
providing an energy source; and
providing a switch fluidly coupled to the negative-pressure source and configured to regulate a therapy pressure of the negative-pressure therapy, the switch comprising:
a housing forming a chamber and having a fluid inlet, a fluid outlet and an ambient pressure opening;
a first conductor electrically coupled to the negative-pressure source;

a second conductor electrically coupled to the energy source, the first conductor and the second conductor being positioned on opposite sides of the ambient pressure opening;

an actuator configured to conduct electricity disposed proximate to the first conductor and the second conductor, the actuator having a first position electrically coupling the first conductor to the second conductor and a second position separated from the first conductor and the second conductor, the actuator configured to move between the first position and the second position in response to a differential between an ambient pressure and a therapy pressure; and operating the negative-pressure source to move the actuator between the first and second positions.

19. The method of claim 18, wherein operation of the negative-pressure source moves the actuator from the first position to the second position, and in response, stopping the operation of the negative-pressure source.

20. The method of claim 18, wherein the operation of the negative-pressure source moves the actuator from the second position to the first position, and in response, illuminating a light emitting diode electrically coupled to the switch.

* * * * *